(12) United States Patent
Xiang et al.

(10) Patent No.: US 11,746,081 B2
(45) Date of Patent: *Sep. 5, 2023

(54) METHODS OF SYNTHESIZING 4-VALYLOXYBUTYRIC ACID

(71) Applicant: XWPHARMA LTD., Grand Cayman (KY)

(72) Inventors: Jia-Ning Xiang, Fremont, CA (US); Hao-Wei Shih, New Taipei (TW); Xiaoming Wu, Wuhan (CN); Xuan Zhang, Wuhan (CN); James Tien, Taoyuan (TW)

(73) Assignee: XWPHARMA LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 17/673,335

(22) Filed: Feb. 16, 2022

(65) Prior Publication Data

US 2022/0234994 A1 Jul. 28, 2022

Related U.S. Application Data

(63) Continuation of application No. 17/351,550, filed on Jun. 18, 2021, now Pat. No. 11,279,669, which is a continuation of application No. PCT/US2020/066047, filed on Dec. 18, 2020.

(30) Foreign Application Priority Data

Dec. 20, 2019 (WO) ................ PCT/CN2019/127065

(51) Int. Cl.
| | |
|---|---|
| C07C 229/08 | (2006.01) |
| C07C 227/18 | (2006.01) |
| C07C 227/20 | (2006.01) |
| C07C 269/06 | (2006.01) |
| C07C 271/22 | (2006.01) |
| C07C 227/16 | (2006.01) |

(52) U.S. Cl.
CPC .......... *C07C 229/08* (2013.01); *C07C 227/16* (2013.01); *C07C 227/18* (2013.01); *C07C 227/20* (2013.01); *C07C 269/06* (2013.01); *C07C 271/22* (2013.01)

(58) Field of Classification Search
None
See application file for complete search history.

(56) References Cited

U.S. PATENT DOCUMENTS

| | | | |
|---|---|---|---|
| 4,370,338 A | 1/1983 | Mizoule | |
| 5,110,797 A | 5/1992 | Ienaga et al. | |
| 6,489,350 B1 | 12/2002 | Benedyk et al. | |
| 7,482,429 B2 | 1/2009 | Albericio et al. | |
| 7,521,455 B2 | 4/2009 | Nagase et al. | |
| 7,960,561 B2 | 6/2011 | Sorensen et al. | |
| 8,529,954 B2 | 9/2013 | Lebon et al. | |
| 9,309,182 B2 | 4/2016 | Tung et al. | |
| 10,457,627 B2 | 10/2019 | Xiang et al. | |
| 10,501,401 B2 | 12/2019 | Xiang et al. | |
| 10,640,451 B2 | 5/2020 | Xiang et al. | |
| 10,774,031 B2 | 9/2020 | Xiang et al. | |
| 11,279,669 B2* | 3/2022 | Xiang | C07C 227/18 |
| 2002/0128301 A1* | 9/2002 | Zhou | C07D 473/32 |
| | | | 548/496 |
| 2004/0214755 A1 | 10/2004 | Albericio et al. | |
| 2005/0182045 A1 | 8/2005 | Nagase et al. | |
| 2006/0122383 A1 | 6/2006 | Zhou et al. | |
| 2006/0210630 A1 | 9/2006 | Liang et al. | |
| 2008/0175873 A1 | 7/2008 | Zhou et al. | |
| 2010/0144869 A1 | 6/2010 | Nudelman et al. | |
| 2011/0178068 A1 | 7/2011 | Almarsson et al. | |
| 2012/0283300 A1 | 11/2012 | Kim et al. | |
| 2016/0052862 A1 | 2/2016 | Frost et al. | |
| 2019/0183806 A1 | 6/2019 | Guillard | |
| 2020/0009076 A1 | 1/2020 | Patel et al. | |

FOREIGN PATENT DOCUMENTS

| | | |
|---|---|---|
| CN | 1422278 | 6/2003 |
| CN | 101511388 | 8/2009 |
| CN | 102076342 | 5/2011 |
| CN | 102834098 | 12/2012 |
| CN | 103370289 | 10/2013 |
| DE | 852392 | 10/1952 |
| EP | 0635265 | 1/1995 |
| EP | 2566462 | 3/2013 |
| FR | 2662695 | 12/1991 |
| JP | 62-270552 | 11/1987 |
| JP | 2002-503673 | 2/2002 |
| JP | 2003-522198 | 7/2003 |

(Continued)

OTHER PUBLICATIONS

International Search Report and Written Opinion for International Application No. PCT/CN2016/099763, dated Jan. 3, 2017, 15 pages.
International Search Report and Written Opinion for International Application No. PCT/CN2017/078873, dated Jan. 9, 2018, 12 pages.
International Search Report and Written Opinion for International Application No. PCT/CN2018/090151, dated Feb. 20, 2019, 14 pages.
International Search Report and Written Opinion for International Application No. PCT/CN2018/097241, dated Apr. 28, 2019, 11 pages.
International Search Report and Written Opinion for International Application No. PCT/CN2018/109115, dated Jul. 8, 2019, 11 pages.
International Search Report and Written Opinion for International Application No. PCT/CN2018/118565, dated Jul. 8, 2019, Apr. 28, 2019, 13 pages.

(Continued)

*Primary Examiner* — Amy C Bonaparte

(57) ABSTRACT

The present disclosure is directed synthetic methods for the preparation of 4-valyloxybutyric acid. The synthetic methods described herein employ a diverse array of protecting group strategies and reaction conditions. Additionally, the present disclosure is directed to compounds useful as synthetic intermediates in the preparation of 4-valyloxybutyric acid.

16 Claims, No Drawings

(56) References Cited

FOREIGN PATENT DOCUMENTS

| | | |
|---|---|---|
| JP | 2004059452 | 2/2004 |
| JP | 2008-526713 | 7/2008 |
| JP | 2013-516465 | 5/2013 |
| RU | 2142800 | 12/1999 |
| WO | 1999/041275 | 8/1999 |
| WO | 1999/051613 | 10/1999 |
| WO | 2004/087169 | 10/2004 |
| WO | 2005/123731 | 12/2005 |
| WO | 2006/038226 | 4/2006 |
| WO | 2009/040331 | 4/2009 |
| WO | 2009/102462 | 8/2009 |
| WO | 2009/137717 | 11/2009 |
| WO | 2010/124046 | 10/2010 |
| WO | 2011/119839 | 9/2011 |
| WO | 2013/019561 | 2/2013 |
| WO | 2013/163244 | 10/2013 |
| WO | 2014/031840 | 2/2014 |
| WO | 2014/078014 | 5/2014 |
| WO | 2014/152263 | 9/2014 |
| WO | 2014/205393 | 12/2014 |
| WO | 2015/057884 | 4/2015 |
| WO | 2015/083129 | 6/2015 |
| WO | 2017/049470 | 3/2017 |
| WO | 2017/050259 | 3/2017 |
| WO | 2018/098472 | 5/2018 |

OTHER PUBLICATIONS

International Search Report and Written Opinion for PCT Application No. PCT/US2020/066047, dated Mar. 23, 2021, 11 pages.
Partial International Search Report and Written Opinion for PCT Application No. PCT/US2021/037830, dated Oct. 6, 2021, 14 pages.
Partial International Search Report and Written Opinion for PCT Application No. PCT/US2021/037909, dated Oct. 4, 2021, 26 pages.
Non-Final Office Action for U.S. Appl. No. 16/831,086, dated Apr. 13, 2020, 8 pages.
Non-Final Office Action for U.S. Appl. No. 16/791,243, dated Apr. 8, 2020, 20 pages.
Ahn et al., "Hapten and Antibody Production for a Sensitive Immunoassay Determining a Human Urinary Metabolite of the Pyrethroid Insecticide Permethrin," Journal of Agricultural and Food Chemistry, Jun. 2004, vol. 52, No. 15, p. 4583-4594.
Search Report for Australia Application No. 2017406159, dated Feb. 28, 2020, 6 pages.
Search Report for Australia Application No. 2016328150, dated Mar. 27, 2020, 4 pages.
Search Report for Russia Application No. 2019134607, dated Feb. 11, 2020, 7 pages (translation).
Durig et al., "Pharmaceutical Technology Report: Water-Soluble Cellulose Ethers as Release Modulators for Ethylcellulose Coatings on Multiparticulates", Annual Meeting of the American Association of Pharmaceutical Scientists, Nov. 2011, 9 pages.
Jiang, et al., "Copper-Catalyzed Aerobic Oxidative Regioselective Thiocyanation of Aromatics and Heteroaromatics", J. Org. Chem. 2017, 82, 18, 9312-9320.
Jimonet et al., "Riluzole series. Synthesis and in vivo "antiglutamate" activity of 6-substituted-2-benzothiazolamines and 3-substituted-2-imino-benzothiazolines", Journal of Medical Chemistry, 1999, vol. 42, p. 2828-2843.
Jordan, et al., Efficient Conversion of Substituted Aryl Thioureas to 2-Aminobenzothiazoles Using Benzyltrimethylammonium Tribromide. J. Org. Chem. 2003, 68, 22, 8693-8696.
Kaname et al., "One-pot copper-catalyzed tandem addition-cyclization of 2-iodoanilines with isoselenocyanates for the practical preparation of 2-aminobenzoselenazoles," Tetrahedron Letters, Jan. 2011, vol. 52, Issue 4, p. 505-508.
Lee et al., "Development of an Immunoassay for the Residues of the Herbicide Bensulfuron-Methyl," Journal of Agricultural and Food Chemistry, Mar. 2002, vol. 50, No. 7, p. 1791-1803.
Luengo et al., "Synthesis and Structure-Activity Relationships of Macrocyclic FKBP Ligands", Bioorganic & Medicinal Chemistry Letters, 1994, vol. 4, No. 2, p. 321-324.
McGeer et al., "Pharmacologic Approaches to the Treatment of Amyotrophic Lateral Sclerosis", Drug Mechanisms and Targets, 2006, vol. 19, No. 1, p. 31-37.
RN 1243631-58-4, STN entry date Sep. 29, 2010.
STN Columbus, Registry Jul. 21, 1990, 128321-03-09, 81055-72-3.
STN Columbus, Registry Dec. 4, 2015, CAS No. 1822708-15-5.
RN 142229-71-8, STN entry date Jul. 3, 1992.
RN 1211588-05-4, STN REG, Mar. 19, 2010.
RN 1354448-66-0, STN REG, Jan. 25, 2012.
RN 1206250-52-3, STN REG, Feb. 12, 2010.
RN 1206250-51-2, STN REG, Feb. 12, 2010.
RN 1206250-54-5, STN REG, Feb. 12, 2010.
RN 1206248-58-9, STN REG, Feb. 12, 2010.
RN 1744-22-5, STN entry date Nov. 16, 1984.
RN 326-45-4, STN entry date Nov. 16, 1984.
RN 747353-64-6, STN REG, Sep. 17, 2004.
RN 60176-62-7, STN entry date Nov. 16, 1984.
RN 60176-63-8, STN REG, Nov. 16, 1984.
RN 60388-38-7, STN entry date Nov. 16, 1984.
CAS Registry No. 238401-16-6 entry date Sep. 10, 1999.
Rothweiler, et al., Probing the ATP-Binding Pocket of Protein Kinase DYRK1A with Benzothiazole Fragment Molecules. J. Med. Chem. 2016, 59, 21, 9814-9824.
Rynearson et al., "2-Aminobenzoxazole ligands of the hepatitis C virus internal ribosome entry site," Bioorganic & Medicinal Chemistry Letters, Aug. 2014, vol. 24, No. 15, p. 3521-3525.
Sankaranarayanan et al., "Naphtho[1,2-d]thiazol-2-ylamine (SKA-31), a new activator of KCa2 and KCa3.1 potassium channels, potentiates the endothelium-derived hyperpolarizing factor response and lowers blood pressure", Molecular Pharmacology, 2009, vol. 75, p. 281-295.
Staldweiser et al., "Combinatorial Solid-Phase Synthesis of Structurally Complex Thiazolylhydantoines," Angewandte Chemie Int. Ed., A Journal of the German Chemical Society, Jun. 1998, vol. 37, No. 10, p. 1402-1404.
Ward et al., "Discovery of an Orally Bioavailable Nki Receptor Antagonist, (2S, 3S)-(2-Methoxy-5-tetrazol-l-ylbenzyl)(2-phenylpiperidin-3-yl)amine (GR203040), with Potent Antiemetic Activity," Journal of Med. Chem., 1995, vol. 38, p. 4985-4992.

* cited by examiner

METHODS OF SYNTHESIZING 4-VALYLOXYBUTYRIC ACID

This application is a continuation of U.S. application Ser. No. 17/351,550 filed on Jun. 18, 2021, now allowed, which is a continuation of PCT International Application No. PCT/US2020/066047 filed on Dec. 18, 2020, which claims the benefit of International Application No. PCT/CN2019/127065 filed on Dec. 20, 2019, each of which is incorporated by reference in its entirety.

BACKGROUND OF THE INVENTION

Narcolepsy is a chronic neurological disorder characterized by excessive daytime sleepiness (EDS), cataplexy, sleep paralysis, hypnagogic hallucinations, and disturbed nocturnal sleep. EDS is present in most cases and is typically the first symptom to manifest. Cataplexy occurs in approximately 70% of patients with narcolepsy.

Gamma-hydroxybutyric acid (GHB) is a naturally occurring central nervous system (CNS) transmitter. The GHB sodium salt, also called sodium oxybate, is currently marketed for the treatment of cataplexy associated with narcolepsy, along with excessive daytime sleepiness. Sodium oxybate has been shown to be highly efficacious, with a ~70% reduction of the total number of cataplexy episodes.

Despite its efficacy in treating EDS and cataplexy associated with narcolepsy, the therapeutic benefits of sodium oxybate are hindered by a sub-optimal pharmacokinetics profile. The deficiencies of sodium oxybate include: (1) variable oral bioavailability and unpredictable drug plasma concentrations resulting from erratic absorption in patients, (2) short plasma half-life ($t_{1/2} < 1$ hr), (3) significant food effect (high-fat meals may significantly delay and hinder absorption of sodium oxybate, (4) unpleasant gastrointestinal side effects caused by high bolus oral dosing, (5) poor patient compliance and inconvenient drug administration due to the twice per night dosage regimen, and (6) risk of hypernatremia (due to significant sodium intake). Because these flaws prevent sodium oxybate from delivering its maximum therapeutic benefit to patients, a persistent need remains for GHB-derived compounds that overcome some or all of these shortcomings, along with methods of manufacture thereof.

SUMMARY OF THE INVENTION

In one aspect, the present disclosure provides a compound of Formula (I-A):

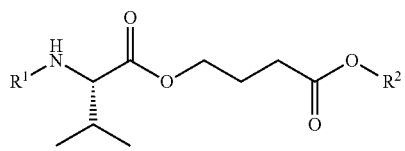

Formula (I-A)

or a pharmaceutically acceptable salt thereof, wherein,
$R^1$ is hydrogen or —C(=O)OCH$_2$(C$_{6-15}$ carbocycle), wherein the C$_{6-15}$ carbocycle is optionally substituted with one or more substituents selected from the group consisting of C$_{1-6}$ alkyl, halogen, hydroxy, alkoxy, and amino; and
$R^2$ is benzyl, allyl, 2-(trimethylsilyl)ethyl, or 2,2,2-trichloroethyl.

In some embodiments, $R^1$ is hydrogen. In some embodiments, $R^1$ is —C(=O)OCH$_2$(C$_{6-15}$ carbocycle).

In some embodiments, the C$_{6-15}$ carbocycle is unsubstituted. In some embodiments, the C$_{6-15}$ carbocycle is substituted with at least one substituent. In some embodiments, the C$_{6-15}$ carbocycle is substituted with at least two substituents.

In some embodiments, $R^2$ is benzyl.

In some embodiments, the compound of Formula (I-A) is represented by the structure:

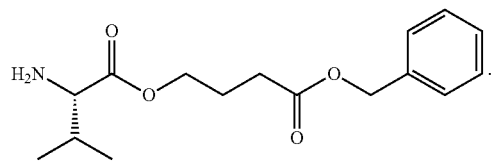 [SMILES: CC(C)[C@H](N)C(=O)OCCCC(=O)OCc1ccccc1]

In some embodiments, the compound of Formula (I-A) is represented by the structure:

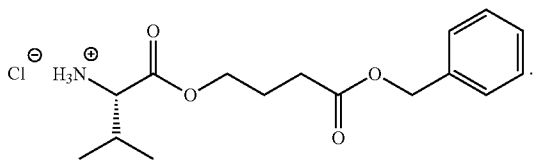 [SMILES: [Cl-] ; CC(C)[C@H]([NH3+])C(=O)OCCCC(=O)OCc1ccccc1]

In some embodiments, the compound of Formula (I-A) is represented by the structure:

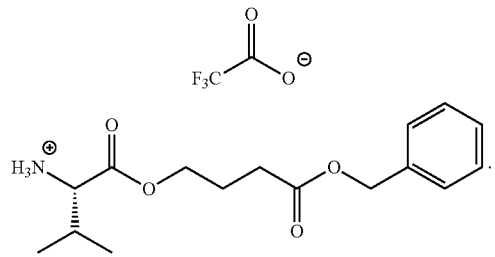

In some embodiments, the compound of Formula (I-A) is represented by the structure:

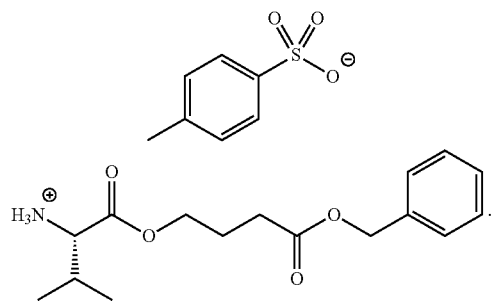

In some embodiments, the compound of Formula (I-A) is represented by the structure:

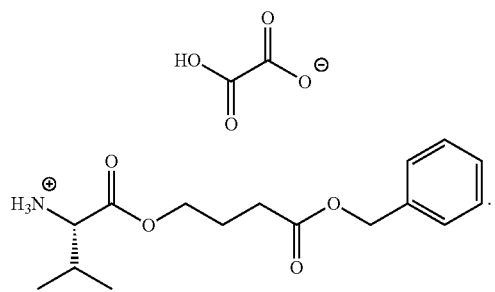

In some embodiments, the compound of Formula (I-A) is represented by the structure:

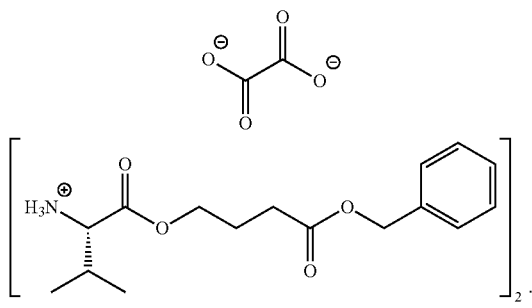

In some embodiments, the compound of Formula (I-A) is represented by the structure:

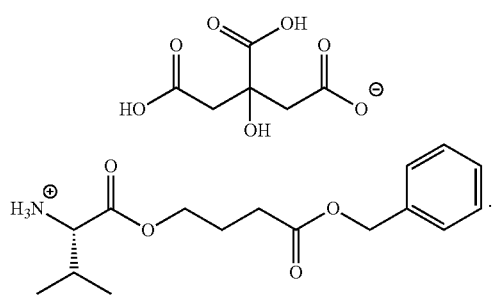

In some embodiments, the compound of Formula (I-A) is represented by the structure:

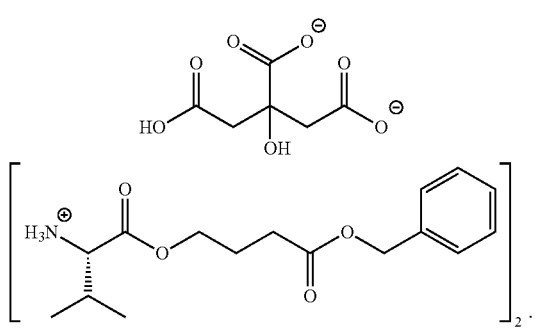

In some embodiments, the compound of Formula (I-A) is represented by the structure:

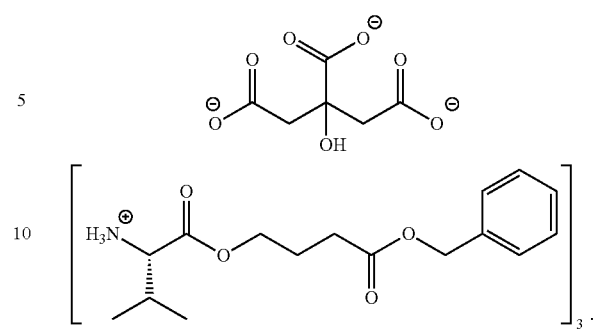

In some embodiments, the compound of Formula (I-A) is represented by the structure:

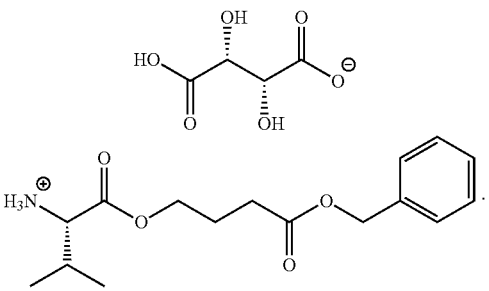

In some embodiments, the compound of Formula (I-A) is represented by the structure:

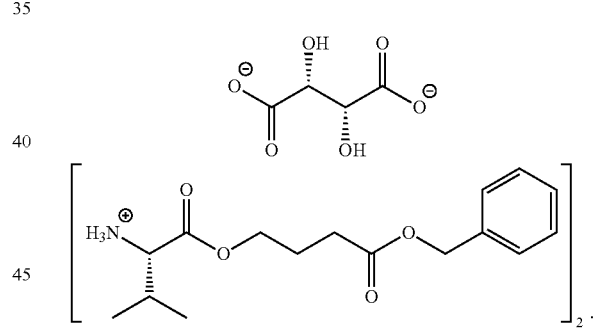

In some embodiments, the compound of Formula (I-A) is represented by the structure:

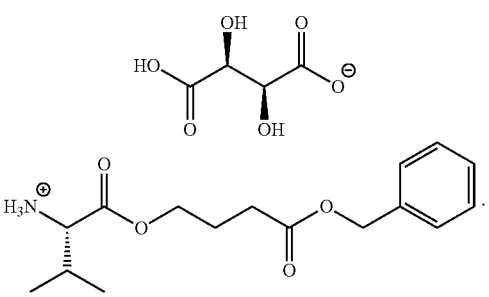

In some embodiments, the compound of Formula (I-A) is represented by the structure:

In some embodiments, the compound of Formula (I-A) is represented by the structure:

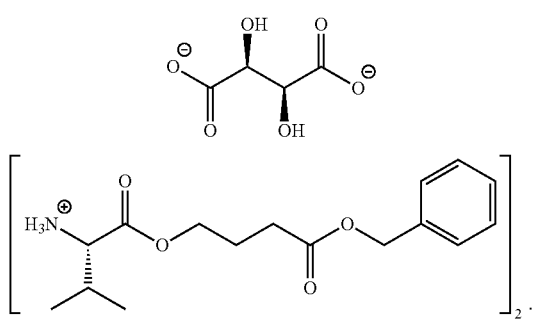

In some embodiments, the compound of Formula (I-A) is represented by the structure:

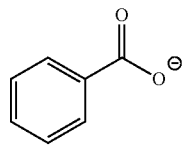

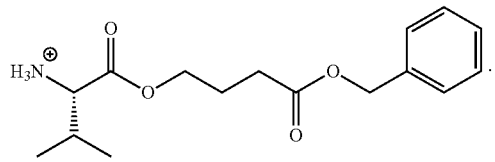

In some embodiments, the compound of Formula (I-A) is represented by the structure:

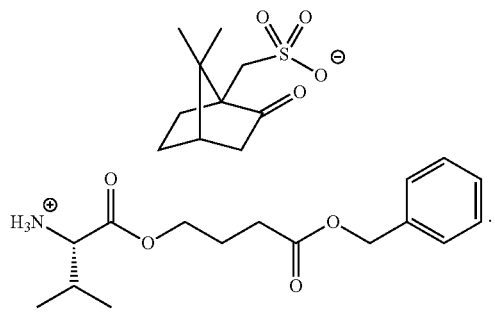

In some embodiments, the compound of Formula (I-A) is represented by the structure:

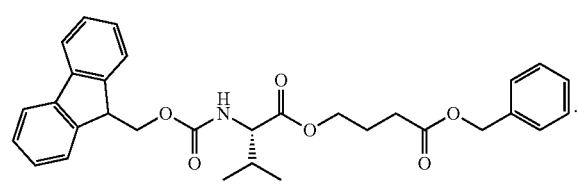 [SMILES: CC(C)[C@H](NC(=O)OCC1c2ccccc2-c2ccccc21)C(=O)OCCCC(=O)OCc1ccccc1]

In some embodiments, the compound of Formula (I-A) is represented by the structure:

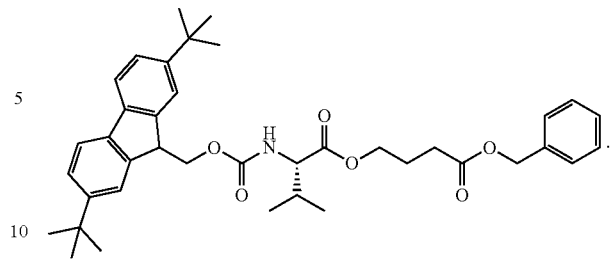

In some embodiments, the compound of Formula (I-A) is represented by the structure:

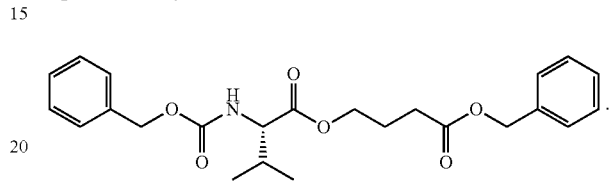

In another aspect, the present disclosure provides a method of preparing a compound of Formula (I-A):

Formula (I-A)

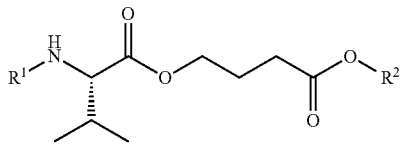

or a pharmaceutically acceptable salt thereof, comprising contacting a compound of Formula (I-B):

Formula (I-B)

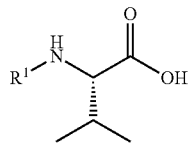

with a compound of Formula (I-C):

Formula (I-C)

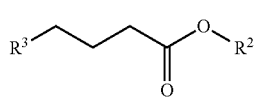

in the presence of a base and a solvent, wherein, $R^1$ is hydrogen or —C(=O)OCH$_2$(C$_{6-15}$ carbocycle), wherein the C$_{6-15}$ carbocycle is optionally substituted with one or more substituents selected from the group consisting of C$_{1-6}$ alkyl, halogen, hydroxy, alkoxy, and amino;

$R^2$ is benzyl, allyl, 2-(trimethylsilyl)ethyl, or 2,2,2-trichloroethyl; and $R^3$ is —OTs, —OMs, or halogen.

In some embodiments, the base is N,N-diisopropylethylamine, triethylamine, potassium carbonate, sodium carbonate, or sodium bicarbonate.

In some embodiments, the solvent is a polar aprotic solvent. In some embodiments, the solvent is acetonitrile, propionitrile, tetrahydrofuran, dichloromethane, dimethylformamide, or dimethyl sulfoxide.

In some embodiments, $R^1$ is —C(=O)OCH$_2$Ph.

In some embodiments, $R^3$ is bromo.

In some embodiments, the solvent is acetonitrile.

In some embodiments, the base is potassium carbonate. In some embodiments, the base is N,N-diisopropylethylamine.

In some embodiments, the compound of Formula (I-B) is represented by the structure:

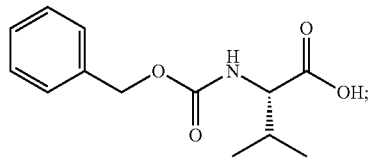 [SMILES: CC(C)[C@H](NC(=O)OCc1ccccc1)C(=O)O]

the compound of Formula (I-C) is represented by the structure:

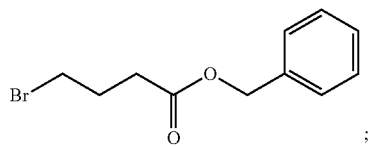 [SMILES: O=C(CCCBr)OCc1ccccc1]

the base is potassium carbonate; and
the solvent is acetonitrile.

In some embodiments, $R^1$ is

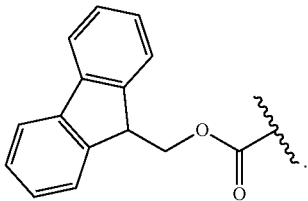 [SMILES: *C(=O)OCC1c2ccccc2-c2ccccc21]

In some embodiments, $R^1$ is

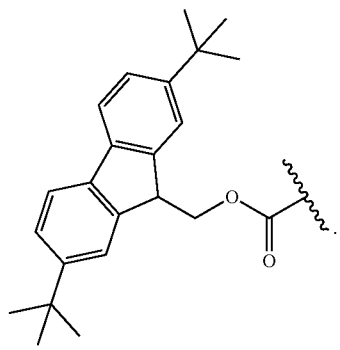 [SMILES: *C(=O)OCC1c2cc(C(C)(C)C)ccc2-c2ccc(C(C)(C)C)cc21]

In some embodiments, the compound of Formula (I-A) is prepared in a synthetic yield of at least 70%.

In some embodiments, the compound of Formula (I-A) is prepared in a synthetic yield of at least 80%.

In some embodiments, the compound of Formula (I-A) is prepared in a synthetic yield of at least 85%.

In another aspect, the present disclosure provides a method of preparing a compound of Formula (I-D):

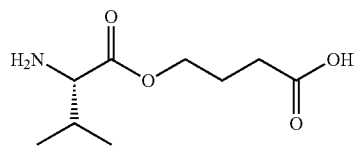

Formula (I-D)

or a pharmaceutically acceptable salt thereof, comprising contacting a compound of Formula (I-E):

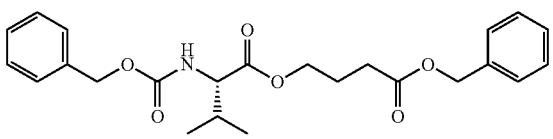

Formula (I-E)

with gaseous hydrogen in the presence of a catalyst and a solvent.

In some embodiments, the catalyst is a Pd-, Ph-, or Pt-based catalyst. In some embodiments, the catalyst is selected from Pd/C, Pd(OH)$_2$, Pd/Al$_2$O$_3$, Pd(OAc)$_2$/Et$_3$SiH, (PPh$_3$)$_3$RhCl, and PtO$_2$. In some embodiments, the catalyst is Pd(OH)$_2$.

In some embodiments, the solvent is selected from methanol, ethanol, diethyl ether, methyl tert-butyl ether, tetrahydrofuran, and dichloromethane. In some embodiments, the solvent is methanol.

In some embodiments, the compound of Formula (I-D) is prepared in a synthetic yield of at least 70%.

In some embodiments, the compound of Formula (I-D) is prepared in a synthetic yield of at least 80%.

In some embodiments, the compound of Formula (I-D) is prepared in a synthetic yield of at least 85%.

In some embodiments, the compound of Formula (I-D) is prepared in substantially pure form without the need for a discrete purification step. In some embodiments, the compound of Formula (I-D) is prepared in at least 90% purity. In some embodiments, the compound of Formula (I-D) is prepared in at least 95% purity.

In another aspect, the present disclosure provides a method of preparing a compound of Formula (I-F):

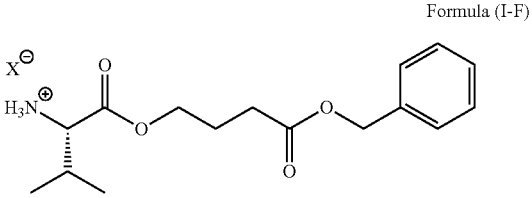

Formula (I-F)

comprising contacting a compound of Formula (I-G):

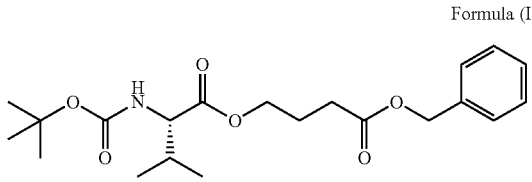

Formula (I-G)

with an acid in the present of a solvent, and then submitting the crude product to a purification method, wherein X is selected from trifluoroacetate and chloride.

In some embodiments, the acid is selected from trifluoroacetic acid and hydrochloric acid.

In some embodiments, the solvent is selected from dichloromethane, ethyl acetate, dioxane, methyl tert-butyl ether, and isopropyl acetate.

In some embodiments, the purification method is selected from trituration, extraction, and recrystallization.

In some embodiments, the acid is hydrochloric acid, the solvent is ethyl acetate, and X is chloride. In some embodiments, the acid is trifluoroacetic acid, the solvent is dichloromethane, and X is trifluoroacetate.

In some embodiments, the purification method is an extraction. In some embodiments, the purification method is a recrystallization.

In another aspect, the present disclosure provides a method of preparing a compound of Formula (I-H):

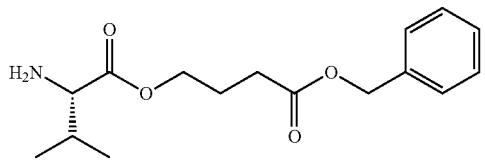

Formula (I-H)

comprising contacting a compound of Formula (I-F):

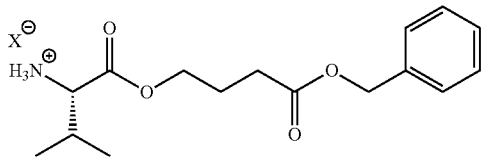

Formula (I-F)

with a base.

In some embodiments, the base is selected from sodium hydroxide, potassium carbonate, sodium carbonate, sodium bicarbonate, ammonium bicarbonate, and ammonium carbonate. In some embodiments, the base is sodium bicarbonate.

In another aspect, the present disclosure provides a method of preparing a compound of Formula (I-D):

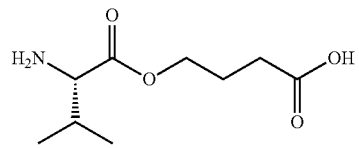

Formula (I-D)

or a pharmaceutically acceptable salt thereof, comprising contacting a compound of Formula (I-H):

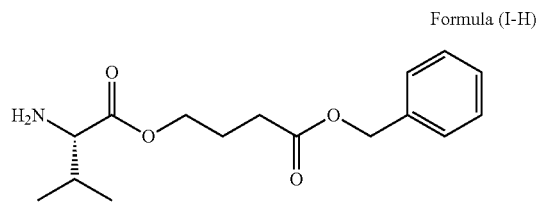 [SMILES: CC(C)[C@H](N)C(=O)OCCCC(=O)OCc1ccccc1]

Formula (I-H)

with gaseous hydrogen in the presence of a catalyst and a solvent.

In some embodiments, the catalyst is a Pd-, Rh-, or Pt-based catalyst. In some embodiments, the catalyst is selected from Pd/C, Pd(OH)$_2$, Pd/Al$_2$O$_3$, Pd(OAc)$_2$/Et$_3$SiH, (PPh$_3$)$_3$RhCl, and PtO$_2$. In some embodiments, the catalyst is Pd(OH)$_2$.

In some embodiments, the solvent is selected from methanol, ethanol, diethyl ether, methyl tert-butyl ether, tetrahydrofuran, and dichloromethane.

In some embodiments, the catalyst is Pd(OH)$_2$ and the solvent is methanol.

In another aspect, the present disclosure provides a method of preparing a compound of Formula (I-H):

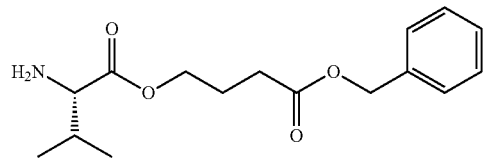

Formula (I-H)

comprising contacting a compound of Formula (I-I):

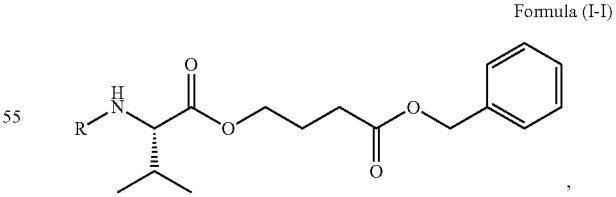

Formula (I-I)

wherein,
R is selected from Fmoc and Dtb-Fmoc; and
the base is selected from piperidine, 1,8-diazabicyclo[5.4.0]undec-7-ene, and N,N-diisopropylethylamine.

In some embodiments, R is Fmoc.

In some embodiments, the base is piperidine.

In another aspect, the present disclosure provides a method of preparing a compound of Formula (I-J):

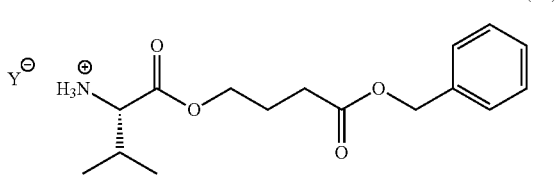

Formula (I-J)

comprising contacting a compound of Formula (I-H):

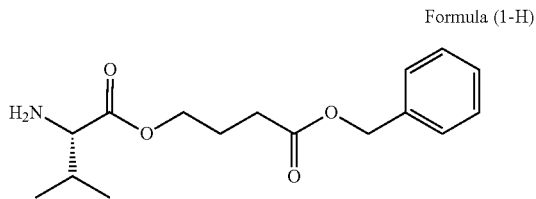 [SMILES: CC(C)[C@H](N)C(=O)OCCCC(=O)OCc1ccccc1]

Formula (I-H)

with an acid in the present of a solvent, and then submitting the crude product to a purification method, wherein Y is selected from p-toluenesulfonate, oxalate, tartrate, malonate, fumarate, and benzoate.

In some embodiments, the acid is selected from p-toluenesulfonic acid, oxalic acid, L-tartaric acid, malonic acid, fumaric acid, and benzoic acid.

In some embodiments, the solvent is selected from dichloromethane, ethyl acetate, dioxane, methyl tert-butyl ether, and isopropyl acetate.

In some embodiments, the purification method is selected from trituration, extraction, and recrystallization.

In another aspect, the present disclosure provides a method of preparing a compound of Formula (I-H):

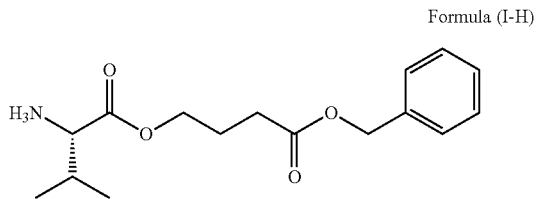 [SMILES: CC(C)[C@H](N)C(=O)OCCCC(=O)OCc1ccccc1]

Formula (I-H)

comprising contacting a compound of Formula (I-J):

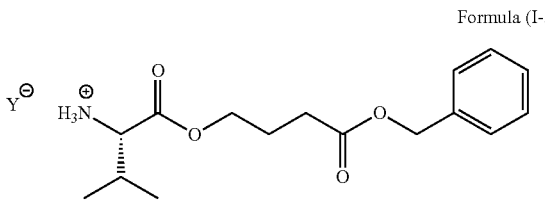

Formula (I-J)

with a base.

In some embodiments, the base is selected from sodium hydroxide, potassium carbonate, sodium carbonate, sodium bicarbonate, ammonium bicarbonate, and ammonium carbonate.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Various features of the present disclosure that are, for brevity, described in the context of a single embodiment, can also be provided separately or in any suitable sub-combination.

As used herein, the term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to, or if appropriate fused to, a parent group. As used herein, the term "optionally substituted" means that the chemical group may have no substituents (i.e. unsubstituted) or may have one or more substituents (i.e. substituted). It is to be understood that substitution at a given atom is limited by valency.

It will be understood by those skilled in the art that substituents can themselves be substituted, if appropriate. Unless specifically states as "unsubstituted," references to chemical moieties herein are understood to include substituted variants. For example, reference to a "heteroaryl" group or moiety implicitly includes both substituted and unsubstituted variants.

Where substituent groups are specified by their conventional chemical formulae, written from left to right, they equally encompass the chemically identical substituents that would result from writing the structure from right to left, e.g., —CH$_2$O— is equivalent to —OCH$_2$—.

As used herein, the term "optionally" means that the subsequently described event or circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

As used herein, the term "$C_{n-m}$" indicates a range of the carbon atoms numbers, wherein n and m are integers, and the range of the carbon atoms numbers includes the endpoints (i.e. n and m) and each integer point in between. For examples, $C_{1-6}$ indicates a range of one to six carbon atoms, including one carbon atom, two carbon atoms, three carbon atoms, four carbon atoms, five carbon atoms and six carbon atoms.

As used herein, the term "alkyl", whether as part of another term or used independently, refers to a saturated hydrocarbon group that may be straight-chain or branched-chain. The term "$C_{n-m}$ alkyl" refers to an alkyl having n to m carbon atoms. In some embodiments, the alkyl group contains 1 to 12, 1 to 8, 1 to 6, 1 to 4, 1 to 3, or 1 to 2 carbon atoms. Examples of alkyl group include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like.

As used herein, the term "carbocycle" refers to a saturated, unsaturated, or aromatic ring in which each atom of the ring is a carbon atom. Carbocycle may include 3- to 10-membered monocyclic rings, 6-to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated, and aromatic bicyclic rings, as valence permits, are included in the definition of carbocycle. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted with one or more substituents such as those substituents described herein.

As used herein, the term "alkoxy", whether as part of another term or used independently, refers to a group of formula —O-alkyl. The term "$C_{n-m}$ alkoxy" means that the alkyl moiety of the alkoxy group has n to m carbon atoms. In some embodiments, the alkyl moiety has 1 to 6, 1 to 4, or 1 to 3 carbon atoms. Examples of alkoxy groups include, but are not limited to, chemical groups such as methoxy, ethoxy, propoxy (e.g., n-propoxy and isopropoxy), t-butoxy, and the like.

As used herein the terms "halo" and "halogen" refer to an atom selected from fluorine, chlorine, bromine and iodine.

As used herein, the term "hydroxyl" refers to a group of formula —OH.

As used herein, the term "amino" refers to a group of formula —$NH_2$.

As used herein, the term "compound" is meant to include all stereoisomers (e.g., enantiomers and diastereomers), geometric isomers, tautomers, and isotopes of the structures depicted. Compounds herein identified by name or structure as one particular tautomeric form are intended to include other tautomeric forms unless otherwise specified.

As used herein, the term "synthetic yield" refers to the molar yield of the synthetic product relative to the limiting reagent.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, carbon-carbon double bonds, and the like can also be present in the compounds described herein, and all such stable isomers are contemplated in the present disclosure.

In some embodiments, the compounds described herein have the (R)-configuration. In some embodiments, the compounds described herein have the (S)-configuration.

Resolution of racemic mixtures of compounds can be carried out by any of numerous methods known in the art. An example method includes fractional recrystallization using a chiral resolving acid, which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the present disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure can also include all isotopes of atoms occurring in the intermediates or final compounds. Isotopes include those atoms having the same atomic number but different mass numbers. For example, isotopes of hydrogen include protium, deuterium and tritium. In some embodiments, the isotope of hydrogen is protium and deuterium. In some embodiments, the hydrogens on the aromatic ring of the compounds include at least one deuterium. In some embodiments, the hydrogens on the aromatic ring of the compounds are all deuteriums.

Compounds

In one aspect, the present disclosure provides a compound of Formula (I-A):

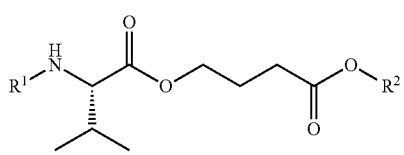

Formula (I-A)

or a pharmaceutically acceptable salt thereof, wherein, $R^1$ is hydrogen, —C(=O)OC(CH$_3$)$_3$, or —C(=O)OCH$_2$(C$_{6-15}$ carbocycle), wherein the C$_{6-15}$ carbocycle is optionally substituted with one or more substituents selected from the group consisting of C$_{1-6}$ alkyl, halogen, hydroxy, alkoxy, and amino; and $R^2$ is benzyl, tert-butyl, allyl, 2-(trimethylsilyl)ethyl, or 2,2,2-trichloroethyl. In some embodiments, $R^1$ is hydrogen. In some embodiments, $R^1$ is hydrogen and $R^2$ is benzyl. In some embodiments, $R^1$ is —C(=O)OCH$_2$(C$_{6-15}$ carbocycle). In some embodiments, $R^1$ is —C(=O)OCH$_2$(C$_{6-15}$ carbocycle) and $R^2$ is benzyl. In some embodiments, the C$_{6-15}$ carbocycle is monocyclic. In some embodiments, the C$_{6-15}$ carbocycle is bicyclic. In some embodiments, the C$_{6-15}$ carbocycle is tricyclic. In some embodiments, the C$_{6-15}$ carbocycle is phenyl.

In some embodiments, the C$_{6-15}$ carbocycle is unsubstituted. In some embodiments, the C$_{6-15}$ carbocycle is substituted with at least one substituent. In some embodiments, the C$_{6-15}$ carbocycle is substituted with at least two substituents. In some embodiments, one or more substituents are C$_{1-6}$ alkyl. In some embodiments, one or more substituents are methyl. In some embodiments, one or more substituents are ethyl. In some embodiments, one or more substituents are n-propyl. In some embodiments, one or more substituents are iso-propyl. In some embodiments, one or more substituents are n-butyl. In some embodiments, one or more substituents are iso-butyl. In some embodiments, one or more substituents are sec-butyl. In some embodiments, one or more substituents are tert-butyl. In some embodiments, one or more substituents are pentyl. In some embodiments, one or more substituents are hexyl. In some embodiments, one or more substituents are bromo. In some embodiments, one or more substituents are chloro. In some embodiments, one or more substituents are fluoro. In some embodiments, one or more substituents are hydroxy. In some embodiments, one or more substituents are alkoxy. In some embodiments, one or more substituents are methoxy. In some embodiments, one or more substituents are ethoxy. In some embodiments, one or more substituents are propoxy. In some embodiments, one or more substituents are amino.

In some embodiments, the compound of Formula (I-A) is represented by the structure:

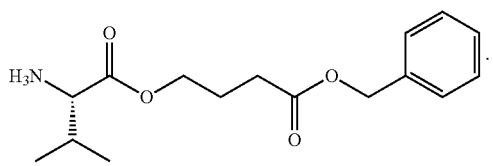 [SMILES: CC(C)[C@H](N)C(=O)OCCCC(=O)OCc1ccccc1]

In some embodiments, the compound of Formula (I-A) is represented by the structure:

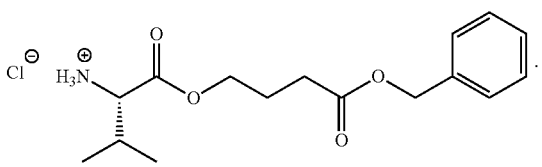 [SMILES: [Cl-] ; CC(C)[C@H]([NH3+])C(=O)OCCCC(=O)OCc1ccccc1]

In some embodiments, the compound of Formula (I-A) is represented by the structure:

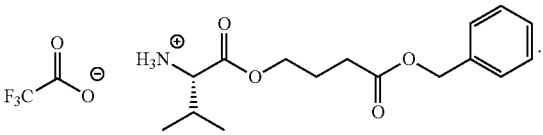 [SMILES: O=C([O-])C(F)(F)F ; CC(C)[C@H]([NH3+])C(=O)OCCCC(=O)OCc1ccccc1]

In some embodiments, the compound of Formula (I-A) is represented by the structure:

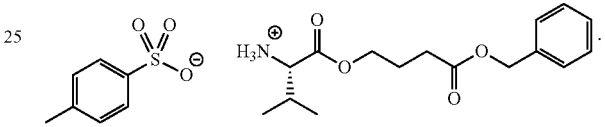

In some embodiments, the compound of Formula (I-A) is represented by the structure:

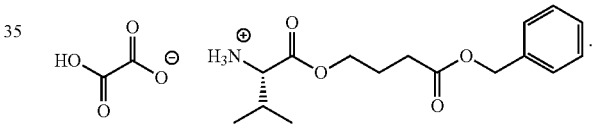

In some embodiments, the compound of Formula (I-A) is represented by the structure:

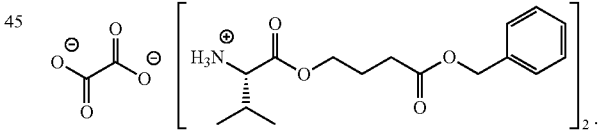

In some embodiments, the compound of Formula (I-A) is represented by the structure:

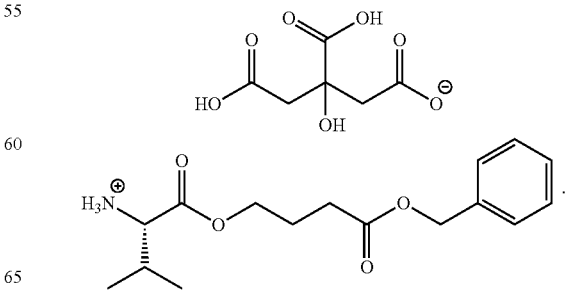

In some embodiments, the compound of Formula (I-A) is represented by the structure:

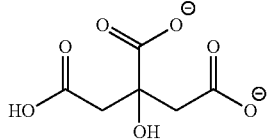

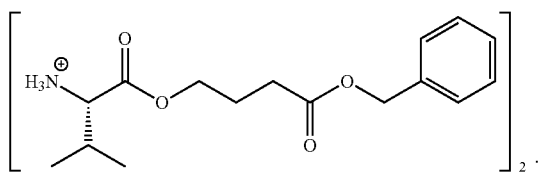

In some embodiments, the compound of Formula (I-A) is represented by the structure:

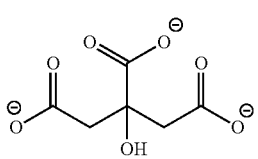

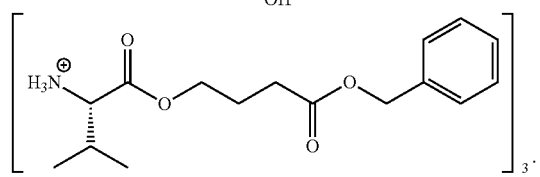

In some embodiments, the compound of Formula (I-A) is represented by the structure:

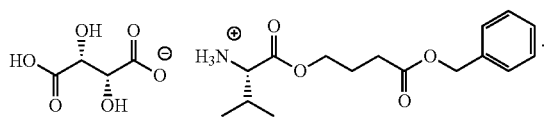 [SMILES: O=C([O-])[C@H](O)[C@@H](O)C(=O)O ; CC(C)[C@H]([NH3+])C(=O)OCCCC(=O)OCc1ccccc1]

In some embodiments, the compound of Formula (I-A) is represented by the structure:

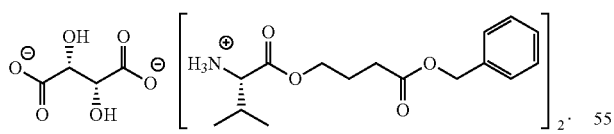

In some embodiments, the compound of Formula (I-A) is represented by the structure:

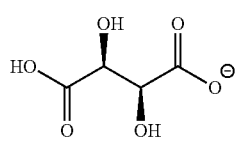

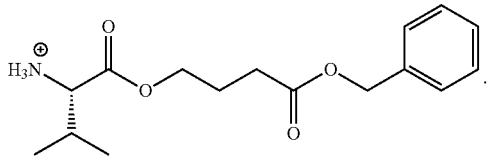

In some embodiments, the compound of Formula (I-A) is represented by the structure:

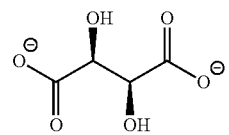

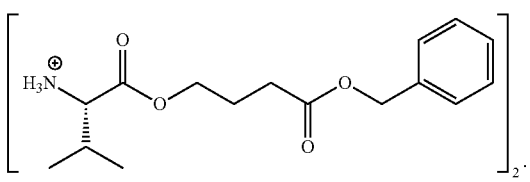

In some embodiments, the compound of Formula (I-A) is represented by the structure:

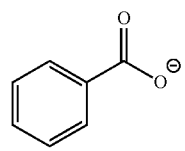

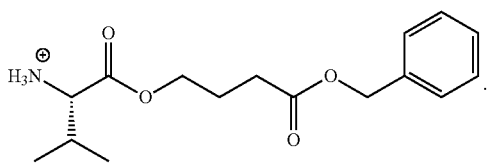

In some embodiments, the compound of Formula (I-A) is represented by the structure:

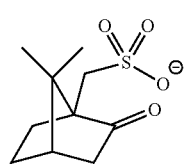

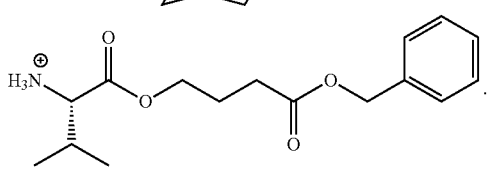

In some embodiments, the compound of Formula (I-A) is represented by the structure:

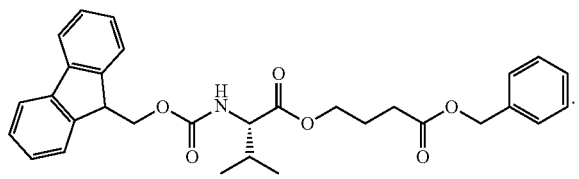 [SMILES: CC(C)[C@H](NC(=O)OCC1c2ccccc2-c2ccccc21)C(=O)OCCCC(=O)OCc1ccccc1]

In some embodiments, the compound of Formula (I-A) is represented by the structure:

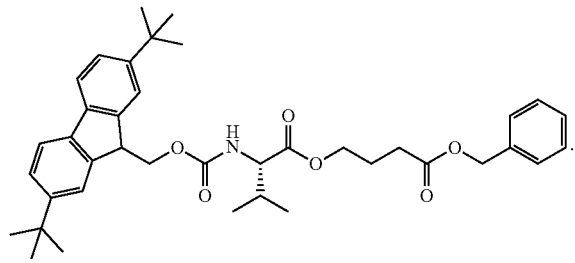 [SMILES: CC(C)[C@H](NC(=O)OCC1c2cc(C(C)(C)C)ccc2-c2ccc(C(C)(C)C)cc21)C(=O)OCCCC(=O)OCc1ccccc1]

In some embodiments, the compound of Formula (I-A) is represented by the structure:

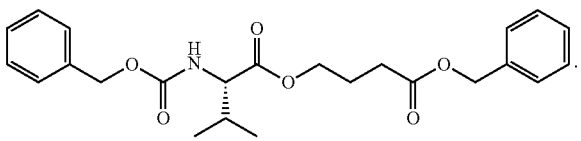 [SMILES: CC(C)[C@H](NC(=O)OCc1ccccc1)C(=O)OCCCC(=O)OCc1ccccc1]

In another aspect, the present disclosure provides a method of preparing a compound of Formula (I-A):

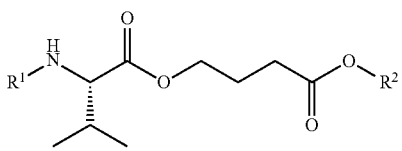

Formula (I-A)

or a pharmaceutically acceptable salt thereof, comprising contacting a compound of Formula (I-B):

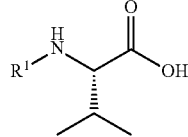

Formula (I-B)

with a compound of Formula (I-C):

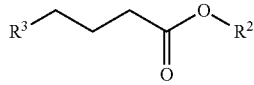

Formula (I-C)

in the presence of a base and a solvent, wherein,
$R^1$ is hydrogen, —C(=O)OC(CH$_3$)$_3$, or —C(=O)OCH$_2$(C$_{6-15}$ carbocycle), wherein the C$_{6-15}$ carbocycle is optionally substituted with one or more substituents selected from the group consisting of C$_{1-6}$ alkyl, halogen, hydroxy, alkoxy, and amino;
$R^2$ is benzyl, tert-butyl, allyl, 2-(trimethylsilyl)ethyl, or 2,2,2-trichloroethyl;
$R^3$ is —OTs, —OMs, or halogen;
the base is N,N-diisopropylethylamine, triethylamine, potassium carbonate, sodium carbonate, or sodium bicarbonate; and
the solvent is acetonitrile, propionitrile, tetrahydrofuran, dichloromethane, dimethylformamide, or dimethyl sulfoxide.

In some embodiments, $R^1$ is hydrogen. In some embodiments, $R^1$ is —C(=O)OCH$_2$Ph. In some embodiments, $R^1$ is —C(=O)OC(CH$_3$)$_3$. In some embodiments, $R^1$ is —C(=O)OCH$_2$(C$_{6-15}$ carbocycle). In some embodiments, the C$_{6-15}$ carbocycle is monocyclic. In some embodiments, the C$_{6-15}$ carbocycle is bicyclic. In some embodiments, the C$_{6-15}$ carbocycle is tricyclic. In some embodiments, the C$_{6-15}$ carbocycle is phenyl.

In some embodiments, the C$_{6-15}$ carbocycle is unsubstituted. In some embodiments, the C$_{6-15}$ carbocycle is substituted with at least one substituent. In some embodiments, the C$_{6-15}$ carbocycle is substituted with at least two substituents. In some embodiments, one or more substituents are C$_{1-6}$ alkyl. In some embodiments, one or more substituents are methyl. In some embodiments, one or more substituents are ethyl. In some embodiments, one or more substituents are n-propyl. In some embodiments, one or more substituents are iso-propyl. In some embodiments, one or more substituents are n-butyl. In some embodiments, one or more substituents are iso-butyl. In some embodiments, one or more substituents are sec-butyl. In some embodiments, one or more substituents are tert-butyl. In some embodiments, one or more substituents are pentyl. In some embodiments, one or more substituents are hexyl. In some embodiments, one or more substituents are bromo. In some embodiments, one or more substituents are chloro. In some embodiments, one or more substituents are fluoro. In some embodiments, one or more substituents are hydroxy. In some embodiments, one or more substituents are alkoxy. In some embodiments, one or more substituents are methoxy. In some embodiments, one or more substituents are ethoxy. In some embodiments, one or more substituents are propoxy. In some embodiments, one or more substituents are amino.

In some embodiments, $R^2$ is benzyl, tert-butyl, or allyl. In some embodiments, $R^2$ is benzyl.

In some embodiments, $R^3$ is —OTs. In some embodiments, $R^3$ is —OMs. In some embodiments, $R^3$ is bromo. In some embodiments, $R^3$ is chloro.

In some embodiments, the solvent is acetonitrile. In some embodiments, the solvent is propionitrile. In some embodiments, the solvent is tetrahydrofuran. In some embodiments, the solvent is dichloromethane. In some embodiments, the solvent is dimethylformamide. In some embodiments, the solvent is dimethyl sulfoxide. In some embodiments, the solvent is toluene.

In some embodiments, the base is N,N-diisopropylethylamine. In some embodiments, the base is triethylamine. In some embodiments, the base is potassium carbonate. In some embodiments, the base is sodium carbonate. In some embodiments, the base is sodium bicarbonate.

In some embodiments, the compound of Formula (I-B) is represented by the structure:

In some embodiments, R¹ is

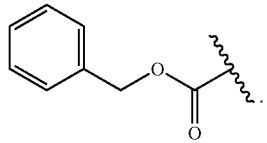

In some embodiments, R¹ is

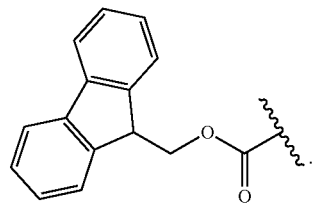

In some embodiments, R¹ is

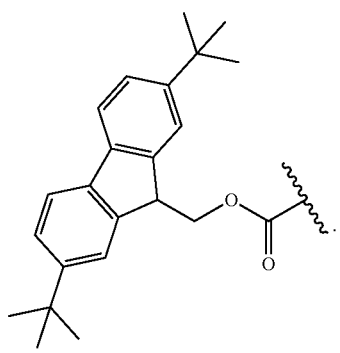

In some embodiments, the compound of Formula (I-A) is prepared in a synthetic yield of at least 90%. In some embodiments, the compound of Formula (I-A) is prepared in a synthetic yield of at least 95%. In some embodiments, the compound of Formula (I-A) is prepared in a synthetic yield of at least 97%. In some embodiments, the compound of Formula (I-A) is prepared in a synthetic yield of at least 99%.

In another aspect, the present disclosure provides a method of preparing a compound of Formula (I-D):

Formula (I-D)

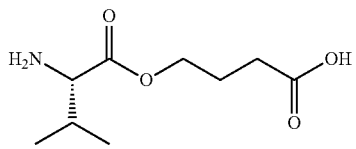

or a pharmaceutically acceptable salt thereof, comprising contacting a compound of Formula (I-E):

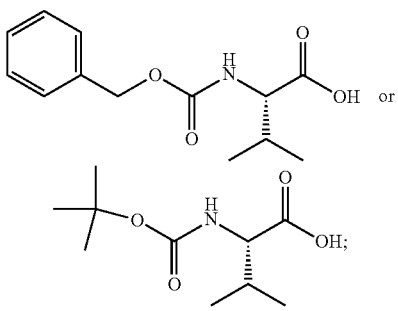

the compound of Formula (I-C) is represented by the structure:

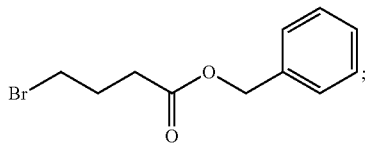 [SMILES: O=C(CCCBr)OCc1ccccc1]

the base is potassium carbonate; and
the solvent is acetonitrile.

In some embodiments, the compound of Formula (I-B) is represented by the structure:

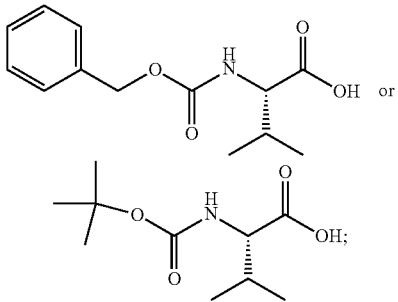

the compound of Formula (I-C) is represented by the structure:

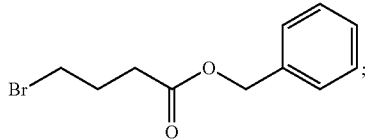 [SMILES: O=C(CCCBr)OCc1ccccc1]

the base is N,N-diisopropylethylamine; and
the solvent is acetonitrile.

In some embodiments, R¹ is

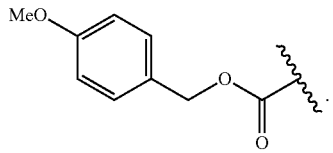 [SMILES: *C(=O)OCc1ccc(OC)cc1]

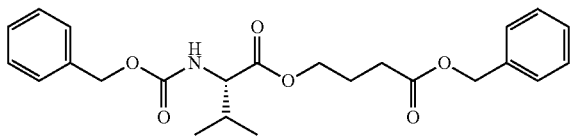

Formula (I-E)

with gaseous hydrogen in the presence of a catalyst and a solvent, wherein, the catalyst is selected from Pd/C, Pd(OH)$_2$, Pd/Al$_2$O$_3$, Pd(OAc)$_2$/Et$_3$SiH, (PPh$_3$)$_3$RhCl, and PtO$_2$; and the solvent is selected from methanol, ethanol, diethyl ether, methyl tert-butyl ether, tetrahydrofuran, and dichloromethane.

In some embodiments, the catalyst is Pd/C. In some embodiments, the catalyst is Pd(OH)$_2$. In some embodiments, the catalyst is Pd/Al$_2$O$_3$. In some embodiments, the catalyst is Pd(OAc)$_2$/Et$_3$SiH, In some embodiments, the catalyst is (PPh$_3$)$_3$RhCl. In some embodiments, the catalyst is PtO$_2$.

In some embodiments, the solvent is methanol. In some embodiments, the solvent is ethanol. In some embodiments, the solvent is diethyl ether. In some embodiments, the solvent is methyl tert-butyl ether. In some embodiments, the solvent is tetrahydrofuran. In some embodiments, the solvent is dichloromethane.

In some embodiments, the compound of Formula (I-D) is prepared in a synthetic yield of at least 90%. In some embodiments, the compound of Formula (I-D) is prepared in a synthetic yield of at least 95%. In some embodiments, the compound of Formula (I-D) is prepared in a synthetic yield of at least 97%. In some embodiments, the compound of Formula (I-D) is prepared in a synthetic yield of at least 99%.

In some embodiments, the compound of Formula (I-D) is prepared in substantially pure form without the need for a discrete purification step. In some embodiments, the compound of Formula (I-D) is prepared in at least 90% purity. In some embodiments, the compound of Formula (I-D) is prepared in at least 95% purity. In some embodiments, the compound of Formula (I-D) is prepared in at least 97% purity. In some embodiments, the compound of Formula (I-D) is prepared in at least 99% purity.

In another aspect, the present disclosure provides a method of preparing a compound of Formula (I-F):

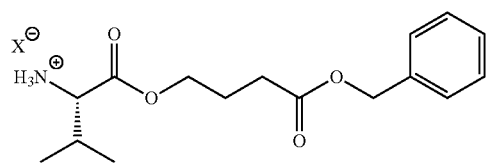

Formula (I-F)

comprising contacting a compound of Formula (I-G):

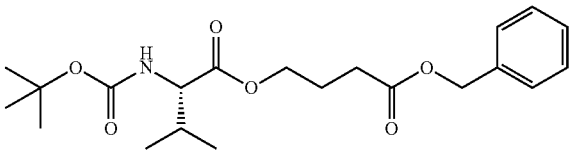

Formula (I-G)

with an acid in the present of a solvent, and then submitting the crude product to a purification method, wherein, the acid is selected from trifluoroacetic acid, hydrochloric acid, and para-toluenesulfonic acid;

the solvent is selected from dichloromethane, ethyl acetate, and methyl tert-butyl ether;

X is selected from trifluoroacetate, chloride, and para-toluenesulfonate; and the purification method is selected from trituration, extraction, and recrystallization.

In some embodiments, the acid is trifluoroacetic acid. In some embodiments, the acid is hydrochloric acid. In some embodiments, the solvent is dichloromethane. In some embodiments, the solvent is ethyl acetate. In some embodiments, X is trifluoroacetate. In some embodiments, X is chloride. In some embodiments, the acid is hydrochloric acid, the solvent is ethyl acetate, and X is chloride. In some embodiments, the acid is trifluoroacetic acid, the solvent is dichloromethane, and X is trifluoroacetate. In some embodiments, the acid is para-toluenesulfonic acid, the solvent is dichloromethane, and X is para-toluenesulfonate.

In some embodiments, the purification method is a trituration. In some embodiments, the purification method is an extraction. In some embodiments, the purification method is a recrystallization.

In another aspect, the present disclosure provides a method of preparing a compound of Formula (I-H):

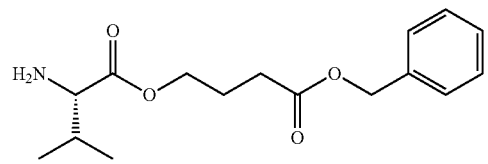

Formula (I-H)

comprising contacting a compound of Formula (I-F):

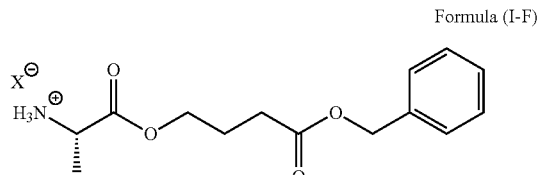

Formula (I-F)

with a base, wherein, the base is selected from sodium hydroxide, potassium carbonate, sodium carbonate, and sodium bicarbonate.

In some embodiments, the base is sodium hydroxide. In some embodiments, the base is potassium carbonate. In some embodiments, the base is sodium carbonate. In some embodiments, the base is sodium bicarbonate.

In another aspect, the present disclosure provides a method of preparing a compound of Formula (I-D):

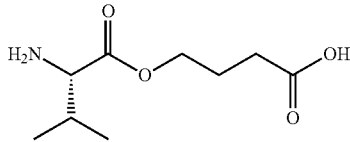

Formula (I-D)

or a pharmaceutically acceptable salt thereof, comprising contacting a compound of Formula (I-H):

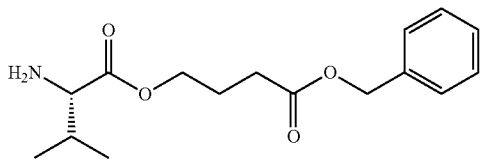

Formula (I-H)

with gaseous hydrogen in the presence of a catalyst and a solvent, wherein, the catalyst is selected from Pd/C, Pd(OH)$_2$, Pd/Al$_2$O$_3$, Pd(OAc)$_2$/Et$_3$SiH, (PPh$_3$)$_3$RhCl, and PtO$_2$; and the solvent is selected from methanol, ethanol, diethyl ether, methyl tert-butyl ether, tetrahydrofuran, and dichloromethane.

In some embodiments, the catalyst is Pd/C. In some embodiments, the catalyst is Pd(OH)$_2$. In some embodiments, the catalyst is Pd/Al$_2$O$_3$. In some embodiments, the catalyst is Pd(OAc)$_2$/Et$_3$SiH, In some embodiments, the catalyst is (PPh$_3$)$_3$RhCl. In some embodiments, the catalyst is PtO$_2$.

In some embodiments, the solvent is methanol. In some embodiments, the solvent is ethanol. In some embodiments, the solvent is diethyl ether. In some embodiments, the solvent is methyl tert-butyl ether. In some embodiments, the solvent is tetrahydrofuran. In some embodiments, the solvent is dichloromethane.

In some embodiments, the catalyst is Pd(OH)$_2$ and the solvent is methanol.

In another aspect, the present disclosure provides a method of preparing a compound of Formula (I-H):

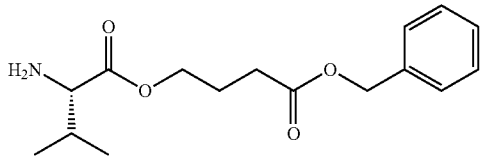

Formula (I-H)

comprising contacting a compound of Formula (I-I):

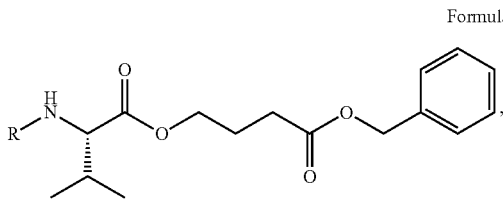

Formula (I-I)

wherein,

R is selected from Fmoc and Dtb-Fmoc; and the base is selected from piperidine, 1,8-diazabicyclo[5.4.0]undec-7-ene, and N,N-diisopropylethylamine.

In some embodiments, R is Fmoc. In some embodiments, R is Dtb-Fmoc.

In some embodiments, the base is piperidine. In some embodiments, the base is 1,8-diazabicyclo[5.4.0]undec-7-ene. In some embodiments, the base is N,N-diisopropylethylamine.

In another aspect, the present disclosure provides a method of preparing a compound of Formula (I-J):

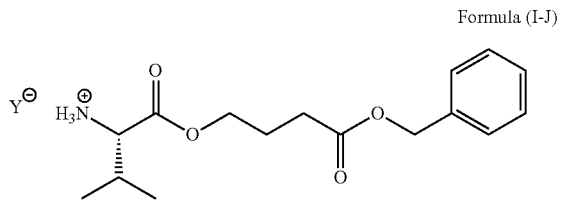

Formula (I-J)

comprising contacting a compound of Formula (I-H):

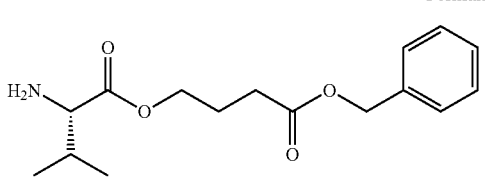

Formula (I-H)

with an acid in the present of a solvent, and then submitting the crude product to a purification method, wherein Y is selected from p-toluenesulfonate, oxalate, tartrate, malonate, fumarate, and benzoate.

In some embodiments, the acid is selected from p-toluenesulfonic acid, oxalic acid, L-tartaric acid, malonic acid, fumaric acid, and benzoic acid. In some embodiments, the acid is p-toluenesulfonic acid. In some embodiments, the acid is oxalic acid. In some embodiments, the acid is L-tartaric acid. In some embodiments, the acid is malonic acid. In some embodiments, the acid is fumaric acid. In some embodiments, the acid is benzoic acid.

In some embodiments, the solvent is selected from dichloromethane, ethyl acetate, dioxane, methyl tert-butyl ether, and isopropyl acetate. In some embodiments, the solvent is dichloromethane. In some embodiments, the solvent is ethyl acetate. In some embodiments, the solvent is dioxane. In some embodiments, the solvent is methyl tert-butyl ether. In some embodiments, the solvent is isopropyl acetate.

In some embodiments, the purification method is selected from trituration, extraction, and recrystallization. In some embodiments, the purification method is trituration. In some embodiments, the purification method is extraction. In some embodiments, the purification method is recrystallization.

In another aspect, the present disclosure provides a method of preparing a compound of Formula (I-H):

Formula (I-H)

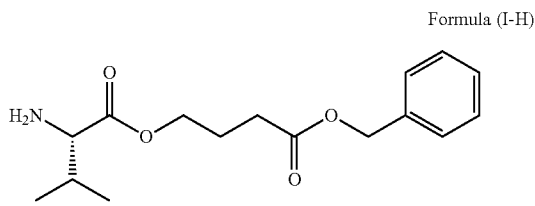 [SMILES: CC(C)[C@H](N)C(=O)OCCCC(=O)OCc1ccccc1]

comprising contacting a compound of Formula (I-J):

Formula (I-J)

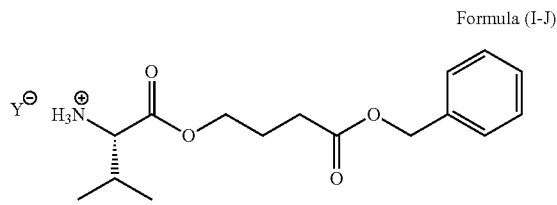

with a base.

In some embodiments, the base is selected from sodium hydroxide, potassium carbonate, sodium carbonate, sodium bicarbonate, ammonium bicarbonate, and ammonium carbonate. In some embodiments, the base is sodium hydroxide. In some embodiments, the base is potassium carbonate. In some embodiments, the base is sodium carbonate. In some embodiments, the base is sodium bicarbonate. In some embodiments, the base is ammonium bicarbonate. In some embodiments, the base is ammonium carbonate.

Synthesis Method

Compounds of the present disclosure, including salts, esters, hydrates, or solvates thereof, can be prepared using any known organic synthesis techniques and can be synthesized according to any of numerous possible synthetic routes.

The reactions for preparing compounds of the present disclosure can be carried out in suitable solvents. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high-performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs, J. Combi. Chem. 2004, 6(6), 874-883, which is incorporated herein by reference in its entirety) and normal phase silica chromatography. Exemplary synthetic schemes are listed below, the abbreviations for the reactants or for the chemical groups of the reactants included in the synthetic schemes are defined in the Examples.

Aspects of the Invention

The invention is further defined by the following aspects.

Aspect 1. A compound of Formula (I-A):

Formula (I-A)

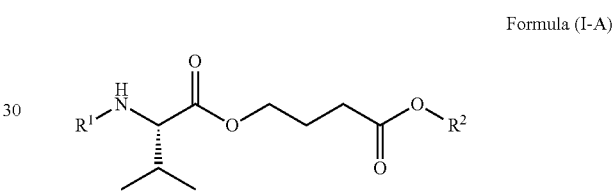

or a pharmaceutically acceptable salt thereof, wherein, $R^1$ is hydrogen or —C(=O)OCH$_2$(C$_{6-15}$ carbocycle), wherein the C$_{6-15}$ carbocycle is optionally substituted with one or more substituents selected from the group consisting of C$_{1-6}$ alkyl, halogen, hydroxy, alkoxy, and amino; and $R^2$ is benzyl, allyl, 2-(trimethylsilyl)ethyl, or 2,2,2-trichloroethyl.

Aspect 2. The compound of aspect 1, wherein $R^1$ is hydrogen.

Aspect 3. The compound of aspect 1, wherein $R^1$ is —C(=O)OCH$_2$(C$_{6-15}$ carbocycle).

Aspect 4. The compound of any one of aspects 1 and 3, wherein the C$_{6-15}$ carbocycle is unsubstituted.

Aspect 5. The compound of any one of aspects 1 and 3 wherein the C$_{6-15}$ carbocycle is substituted with at least one substituent.

Aspect 6. The compound of any one of aspects 1, 3, and 5, wherein the C$_{6-15}$ carbocycle is substituted with at least two substituents.

Aspect 7. The compound of any one of aspects 1 to 6, wherein $R^2$ is benzyl.

Aspect 8. The compound of aspect 1, wherein the compound of Formula (I-A) is represented by the structure:

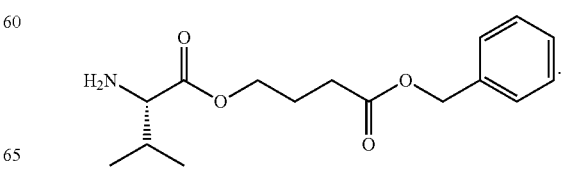

Aspect 9. The compound of aspect 1, wherein the compound of Formula (I-A) is represented by the structure:

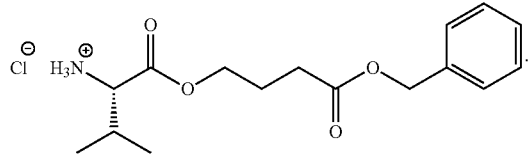 [SMILES: [Cl-] ; CC(C)[C@H]([NH3+])C(=O)OCCCC(=O)OCc1ccccc1]

Aspect 10. The compound of aspect 17, wherein the compound of Formula (I-A) is represented by the structure:

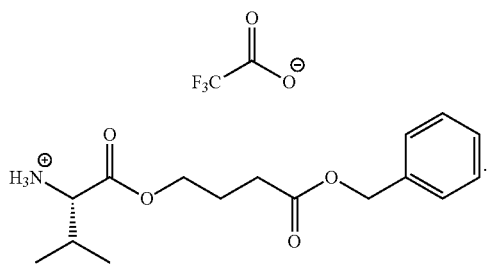

Aspect 11. The compound of aspect 1, wherein the compound of Formula (I-A) is represented by the structure:

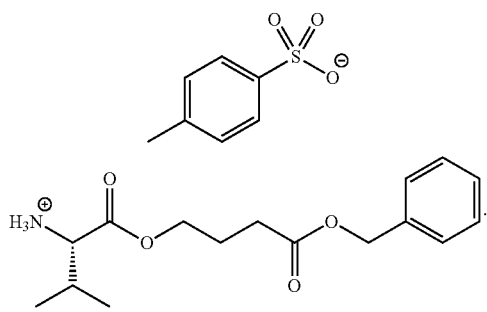

Aspect 12. The compound of aspect 1, wherein the compound of Formula (I-A) is represented by the structure:

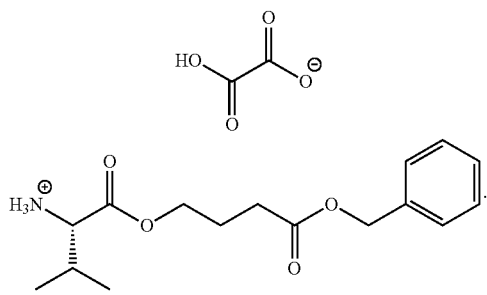

Aspect 13. The compound of aspect 1, wherein the compound of Formula (I-A) is represented by the structure:

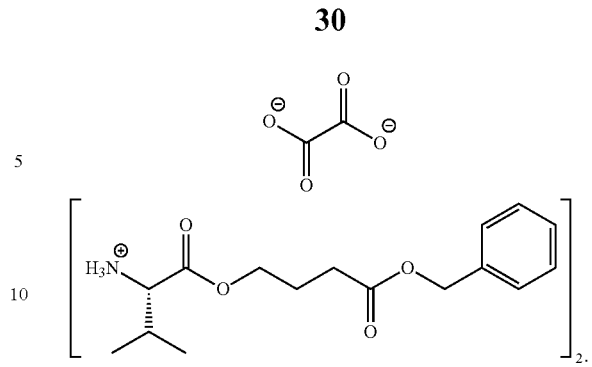

Aspect 14. The compound of aspect 1, wherein the compound of Formula (I-A) is represented by the structure:

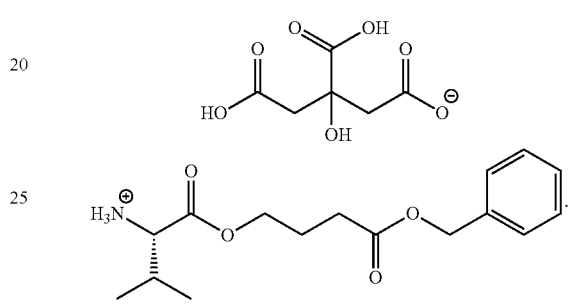

Aspect 15. The compound of aspect 1, wherein the compound of Formula (I-A) is represented by the structure:

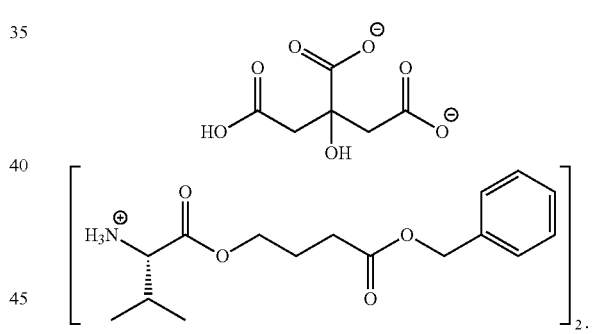

Aspect 16. The compound of aspect 1, wherein the compound of Formula (I-A) is represented by the structure:

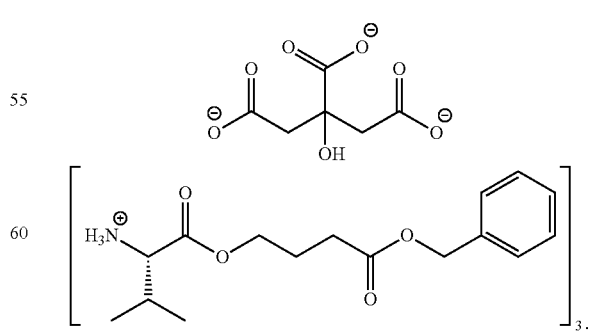

Aspect 17. The compound of aspect 1, wherein the compound of Formula (I-A) is represented by the structure:

Aspect 18. The compound of aspect 1, wherein the compound of Formula (I-A) is represented by the structure:

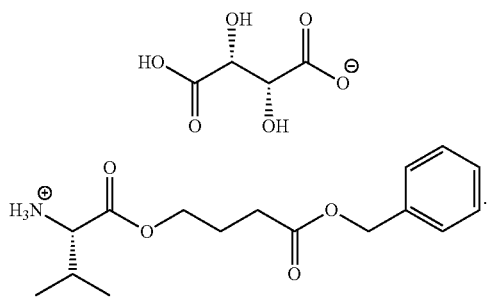

Aspect 19. The compound of aspect 1, wherein the compound of Formula (I-A) is represented by the structure:

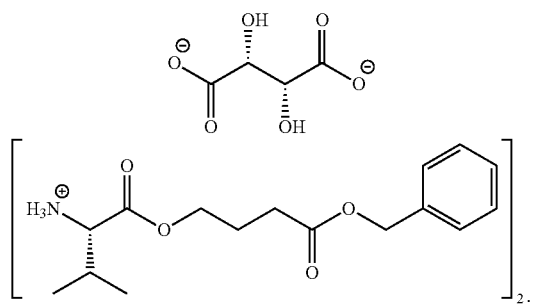

Aspect 20. The compound of aspect 1, wherein the compound of Formula (I-A) is represented by the structure:

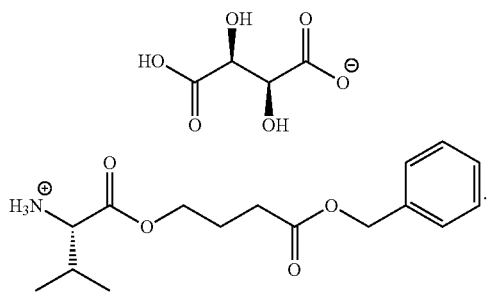

Aspect 21. The compound of aspect 1, wherein the compound of Formula (I-A) is represented by the structure:

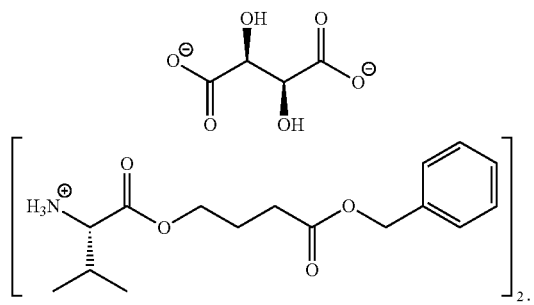

Aspect 22. The compound of aspect 1, wherein the compound of Formula (I-A) is represented by the structure:

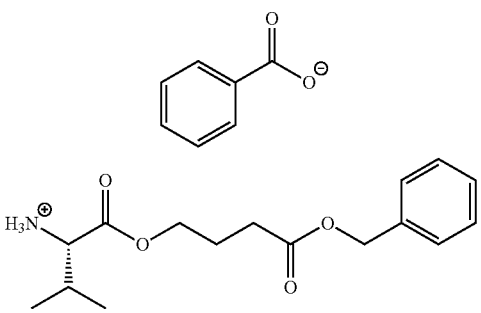

Aspect 23. The compound of aspect 1, wherein the compound of Formula (I-A) is represented by the structure:

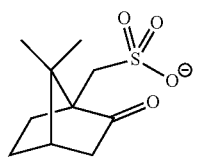

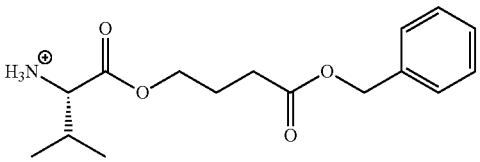

Aspect 24. The compound of aspect 1, wherein the compound of Formula (I-A) is represented by the structure:

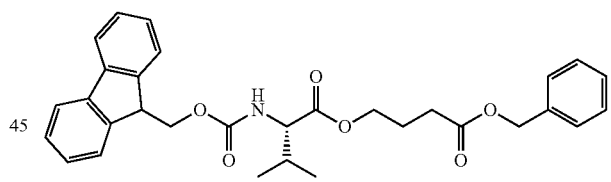

Aspect 25. The compound of aspect 1, wherein the compound of Formula (I-A) is represented by the structure:

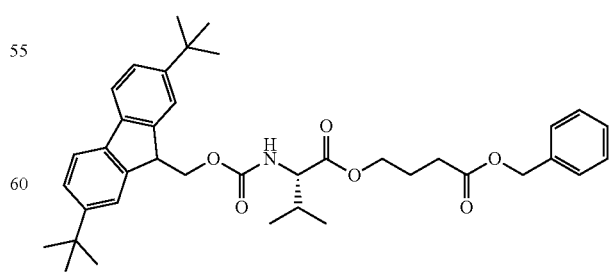

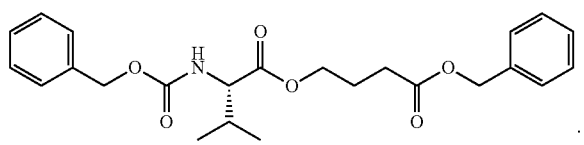 [SMILES: CC(C)[C@H](NC(=O)OCc1ccccc1)C(=O)OCCCC(=O)OCc1ccccc1]

Aspect 26. A method of preparing a compound of Formula (I-A):

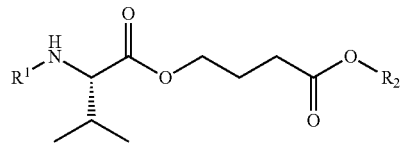

Formula (I-A)

or a pharmaceutically acceptable salt thereof, comprising: contacting a compound of Formula (I-B):

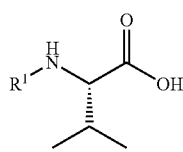

Formula (I-B)

with a compound of Formula (I-C):

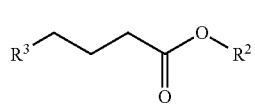

Formula (I-C)

in the presence of a base and a solvent, wherein,
$R^1$ is hydrogen or —C(=O)OCH$_2$(C$_{6-15}$ carbocycle), wherein the C$_{6-15}$carbocycle is optionally substituted with one or more substituents selected from the group consisting of C$_{1-6}$alkyl, halogen, hydroxy, alkoxy, and amino;
$R^2$ is benzyl, allyl, 2-(trimethylsilyl)ethyl, or 2,2,2-trichloroethyl; and
$R^3$ is —OTs, —OMs, or halogen.

Aspect 27. The method of aspect 26, wherein the base is N,N-diisopropylethylamine, triethylamine, potassium carbonate, sodium carbonate, or sodium bicarbonate.

Aspect 28. The method of any one of aspects 26 to 27, wherein the solvent is a polar aprotic solvent.

Aspect 29. The method of any one of aspects 26 to 28, wherein the solvent is acetonitrile, propionitrile, tetrahydrofuran, dichloromethane, dimethylformamide, or dimethyl sulfoxide.

Aspect 30. The method of any one of aspects 26 to 29, wherein $R^1$ is —C(=O)OCH$_2$Ph.

Aspect 31. The method of any one of aspects 26 to 30, wherein $R^3$ is bromo.

Aspect 32. The method of any one of aspects 26 to 31, wherein the solvent is acetonitrile.

Aspect 33. The method of any one of aspects 26 to 32, wherein the base is potassium carbonate.

Aspect 34. The method of any one of aspects 26 to 32, wherein the base is N,N-diisopropylethylamine.

Aspect 35. The method of any one of aspects 26 to 33, wherein,
the compound of Formula (I-B) is represented by the structure:

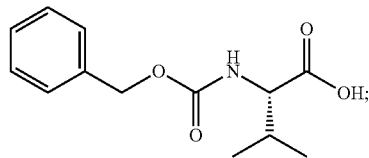 [SMILES: CC(C)[C@H](NC(=O)OCc1ccccc1)C(=O)O]

the compound of Formula (I-C) is represented by the structure:

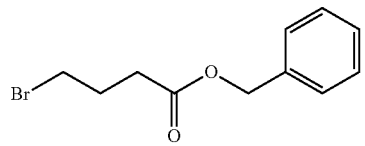

the base is potassium carbonate; and
the solvent is acetonitrile.

Aspect 36. The method of any one of aspects 26 to 29 and 31 to 34, wherein $R^1$ is

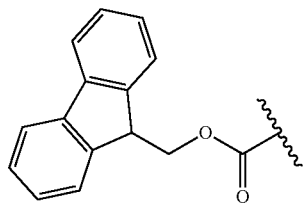

Aspect 37. The method of any one of aspects 26 to 29 and 31 to 34, wherein $R^1$ is

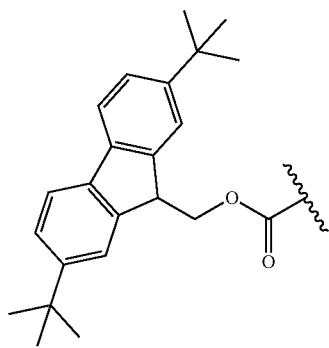

Aspect 38. The method of any one of aspects 26 to 37, wherein the compound of Formula (I-A) is prepared in a synthetic yield of at least 70%.

Aspect 39. The method of any one of aspects 26 to 38, wherein the compound of Formula (I-A) is prepared in a synthetic yield of at least 80%.

Aspect 40. The method of any one of aspects 26 to 39, wherein the compound of Formula (I-A) is prepared in a synthetic yield of at least 85%.

Aspect 41. A method of preparing a compound of Formula (I-D):

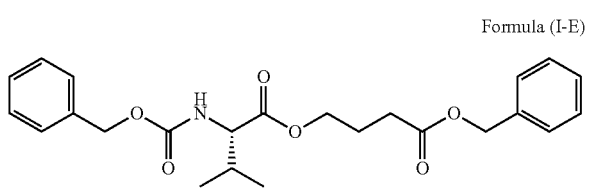 [SMILES: CC(C)[C@H](NC(=O)OCc1ccccc1)C(=O)OCCCC(=O)OCc1ccccc1]

Formula (I-D)

or a pharmaceutically acceptable salt thereof, comprising contacting a compound of Formula (I-E):

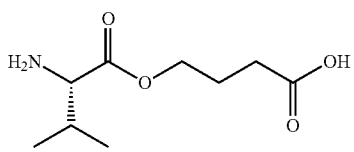

Formula (I-E)

with gaseous hydrogen in the presence of a catalyst and a solvent.

Aspect 42. The method of aspect 41, wherein, the catalyst is a Pd-, Rh-, or Pt-based catalyst.

Aspect 43. The method of any one of aspects 41 to 42, wherein the catalyst is selected from Pd/C, Pd(OH)$_2$, Pd/Al$_2$O$_3$, Pd(OAc)$_2$/Et$_3$SiH, (PPh$_3$)$_3$RhCl, and PTO$_2$.

Aspect 44. The method of any one of aspects 41 to 43, wherein the catalyst is Pd(OH)$_2$.

Aspect 45. The method of any one of aspects 41 to 44, wherein the solvent is selected from methanol, ethanol, diethyl ether, methyl tert-butyl ether, tetrahydrofuran, and dichloromethane.

Aspect 46. The method of any one of aspects 41 to 45, wherein the solvent is methanol.

Aspect 47. The method of any one of aspects 41 to 46, wherein the compound of Formula (I-D) is prepared in a synthetic yield of at least 70%.

Aspect 48. The method of any one of aspects 41 to 47, wherein the compound of Formula (I-D) is prepared in a synthetic yield of at least 80%.

Aspect 49. The method of any one of aspects 41 to 48, wherein the compound of Formula (I-D) is prepared in a synthetic yield of at least 85%.

Aspect 50. The method of any one of aspects 41 to 49, wherein the compound of Formula (I-D) is prepared in at least 90% purity.

Aspect 51. The method of any one of aspects 41 to 50, wherein the compound of Formula (I-D) is prepared in at least 95% purity.

Aspect 52. The method of any one of aspects 41 to 51, wherein the compound of Formula (I-D) is prepared without the need for a discrete purification step.

Aspect 53. A method of preparing a compound of Formula (I-F):

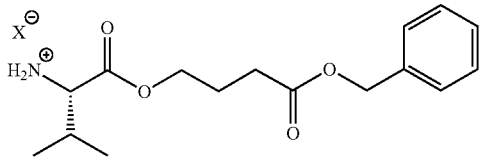

Formula (I-F)

comprising contacting a compound of Formula (I-G):

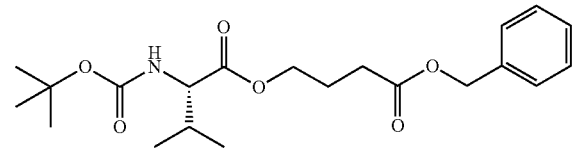

Formula (I-G)

with an acid in the present of a solvent, and then submitting the crude product to a purification method, wherein X is selected from trifluoroacetate and chloride.

Aspect 54. The method of aspect 53, wherein the acid is selected from trifluoroacetic acid and hydrochloric acid.

Aspect 55. The method of any one of aspects 52 to 54, wherein the solvent is selected from dichloromethane, ethyl acetate, dioxane, methyl tert-butyl ether, and isopropyl acetate.

Aspect 56. The method of any one of aspects 53 to 55, wherein the purification method is selected from trituration, extraction, and recrystallization.

Aspect 57. The method of any one of aspects 53 to 56, wherein the acid is hydrochloric acid, the solvent is ethyl acetate, and X is chloride.

Aspect 58. The method of any one of aspects 53 to 56, wherein the acid is trifluoroacetic acid, the solvent is dichloromethane, and X is trifluoroacetate.

Aspect 59. The method of any one of aspects 53 to 58, wherein the purification method is an extraction.

Aspect 60. The method of any one of aspects 53 to 58, wherein the purification method is a recrystallization.

Aspect 61. A method of preparing a compound of Formula (I-H):

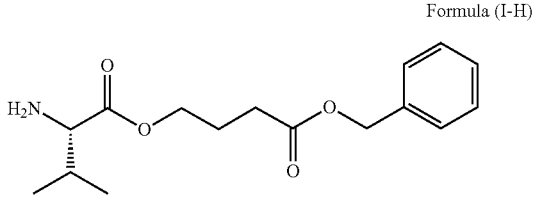

Formula (I-H)

comprising contacting a compound of Formula (I-F):

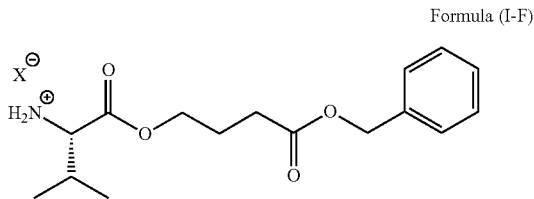

Formula (I-F)

with a base.

Aspect 62. The method of aspect 61, wherein the base is selected from sodium hydroxide, potassium carbonate, sodium carbonate, sodium bicarbonate, ammonium bicarbonate, and ammonium carbonate.

Aspect 63. The method of any one of aspects 61 to 62, wherein the base is sodium bicarbonate.

Aspect 64. A method of preparing a compound of Formula (I-D):

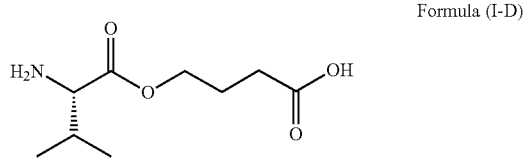

Formula (I-D)

or a pharmaceutically acceptable salt thereof, comprising contacting a compound of Formula (I-H):

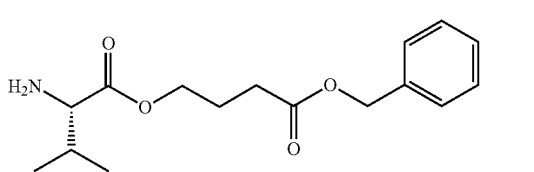

Formula (I-H)

with gaseous hydrogen in the presence of a catalyst and a solvent.

Aspect 65. The method of aspect 64, wherein, the catalyst is a Pd-, Rh-, or Pt-based catalyst.

Aspect 66. The method of any one of aspects 64 to 65, wherein the catalyst is selected from Pd/C, Pd(OH)$_2$, Pd/Al$_2$O$_3$, Pd(OAc)$_2$/Et$_3$SiH, (PPh$_3$)$_3$RhCl, and PtO$_2$.

Aspect 67. The method of any one of aspects 64 to 66, wherein the catalyst is Pd(OH)$_2$.

Aspect 68. The method of any one of aspects 64 to 67, wherein the solvent is selected from methanol, ethanol, diethyl ether, methyl tert-butyl ether, tetrahydrofuran, and dichloromethane.

Aspect 69. The method of any one of aspects 64 to 68, wherein the catalyst is Pd(OH)$_2$ and the solvent is methanol.

Aspect 70. A method of preparing a compound of Formula (I-H):

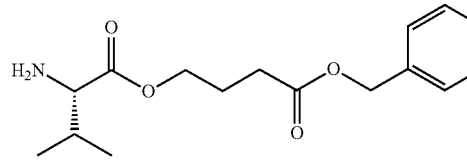

Formula (I-H)

comprising contacting a compound of Formula (I-I):

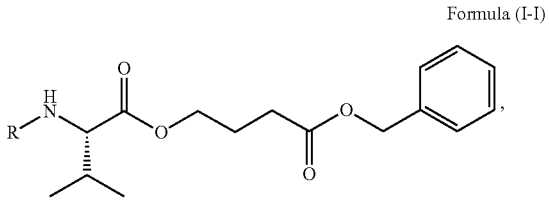

Formula (I-I)

wherein,
R is selected from Fmoc and Dtb-Fmoc; and
the base is selected from piperidine, 1,8-diazabicyclo [5.4.0]undec-7-ene, and N,N-diisopropylethylamine.

Aspect 71. The method of aspect 70, wherein R is Fmoc.

Aspect 72. The method of any one of aspects 70 to 71, wherein the base is piperidine.

Aspect 73. A method of preparing a compound of Formula (I-J):

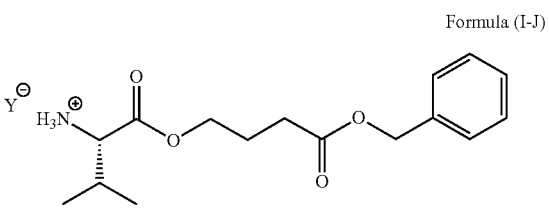

Formula (I-J)

comprising contacting a compound of Formula (I-H):

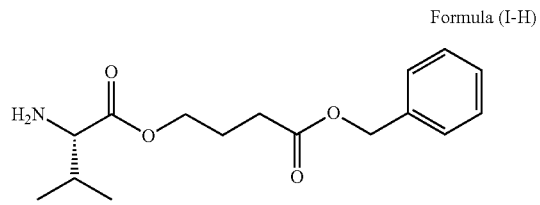 [SMILES: CC(C)[C@H](N)C(=O)OCCCC(=O)OCc1ccccc1]

Formula (I-H)

with an acid in the present of a solvent, and then submitting the crude product to a purification method, wherein Y is selected from p-toluenesulfonate, oxalate, tartrate, malonate, fumarate, and benzoate.

Aspect 74. The method of aspect 73, wherein the acid is selected from p-toluenesulfonic acid, oxalic acid, L-tartaric acid, malonic acid, fumaric acid, and benzoic acid.

Aspect 75. The method of aspects 73 to 74, wherein the solvent is selected from dichloromethane, ethyl acetate, dioxane, methyl tert-butyl ether, and isopropyl acetate.

Aspect 76. The method of any one of aspects 73 to 75, wherein the purification method is selected from trituration, extraction, and recrystallization.

Aspect 77. A method of preparing a compound of Formula (I-H):

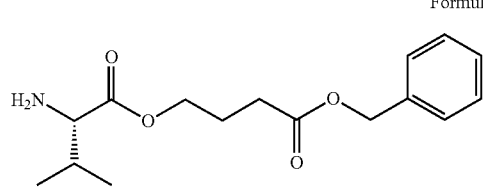

Formula (I-H)

comprising contacting a compound of Formula (I-J):

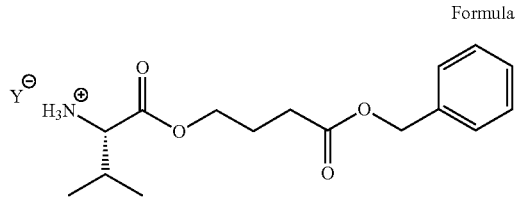

Formula (I-J)

with a base.

Aspect 78. The method of aspect 77, wherein the base is selected from sodium hydroxide, potassium carbonate, sodium carbonate, sodium bicarbonate, ammonium bicarbonate, and ammonium carbonate.

EXAMPLES

The following examples are presented to illustrate the present disclosure. They are not intended to be limiting in any matter.

Unless stated otherwise, all reagents were purchased from commercial suppliers without further purification. Solvent drying by standard methods was employed when necessary. The plates used for thin-layer chromatography (TLC) were E. Merck silica gel 60F254 (0.24 nm thickness) precoated on aluminum plates, and then visualized under UV light (365 nm and 254 nm) or through staining with a 5% of dodecamolybdophosphoric acid in ethanol and subsequent heating. Column chromatography was performed using silica gel (200-400 mesh) from commercial suppliers. $^1$H NMR spectra were recorded on an Agilent 400-MR NMR spectrometer (400.00 MHz for $^1$H) at room temperature. Solvent signal was used as reference for $^1$H NMR (CDCl$_3$, 7.26 ppm; CD$_3$OD, 3.31 ppm; d$_6$-DMSO, 2.50 ppm; D$_2$O, 4.79 ppm). The following abbreviations were used to explain the multiplicities: s=singlet, d=doublet, t=triplet, q=quartet, br.s.=broad singlet, dd=double doublet, td=triple doublet, dt=double triplet, dq=double quartet, m=multiplet. Other abbreviations used in the experimental details are as follows: Ar=aryl, Boc=tert-butyloxy carbonyl, Bn=Benzyl, δ=chemical shift in parts per million downfield from tetramethylsilane, DCC=dicyclohexylcarbodiimide, DCM=dichloromethane, DIPEA=diisopropylethylamine, DMAP=4-(dimethylamino)pyridine, DMF=N,N-dimethylformamide, EA=ethyl acetate, Et=ethyl, HATU=1-[bis(dimethylamino)methylene]-1H-1,2,3-triazolo[4,5-b]pyridinium 3-oxid hexafluorophosphate, Hex.=hexanes, Hz=hertz, J=coupling constant (in NMR), Me=methyl, min= minute (s), NMR=nuclear magnetic resonance, Ph=phenyl, ppm=parts per million, iPr=isopropyl, TBAF=tetrabutylammonium fluoride, tert=tertiary, TFA=trifluoroacetic acid, THF=tetrahydrofuran, TLC=thin-layer chromatography.

Example 1

Synthesis of (S)-4-(2-amino-3-methylbutanoyloxy)butanoic acid

Step 1: Preparation of (S)-4-hydroxybutyl 2-(tert-butoxycarbonylamino)-3-methylbutanoate (1)

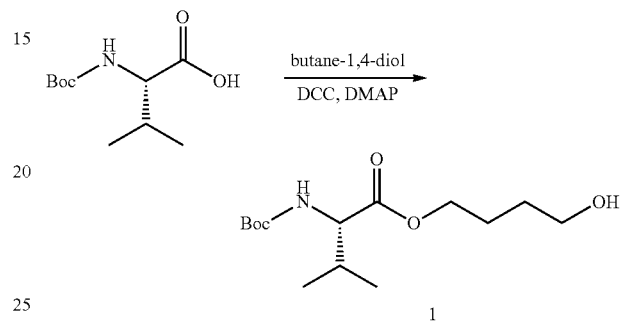

(S)-2-(tert-Butoxycarbonylamino)-3-methylbutanoic acid (1 g, 4.61 mmol), DCC (1044 mg, 5.07 mmol) and DMAP (10 mg) were added to a stirred solution of butane-1,4-diol (829 mg, 9.21 mmol) in DCM (20 mL). The reaction was stirred at 25° C. for 16 h. After that, the reaction mixture was diluted with saturated aqueous NH$_4$Cl (10 mL) and stirred for five minutes. The aqueous phase was separated and extracted with DCM (10 mL). The combined organic phase was washed with saturated brine (15 mL), dried over anhydrous Na$_2$SO$_4$, and evaporated. The residue was purified by a silica gel flash column with Hex/EA=5:1 to yield (S)-4-hydroxybutyl 2-(tert-butoxycarbonylamino)-3-methylbutanoate 1 (700 mg, 53%) as a colorless oil. $^1$H NMR was performed at 400 MHz with CDCl$_3$ as solvent to characterize the titled compound, results are as follows: δ=5.07 (d, J=8.8 Hz, 1H), 4.16-4.11 (m, 3H), 3.62 (t, J=6.2 Hz, 2H), 2.32 (br. s., 1H), 2.12-2.04 (m, 1H), 1.75-1.68 (m, 2H), 1.62-1.56 (m, 2H), 1.40 (s, 9H), 0.92 (d, J=7.2 Hz, 3H), 0.85 (d, J=7.2 Hz, 3H).

Step 2: Preparation of (S)-4-(2-(tert-butoxycarbonylamino)-3-methylbutanoyloxy)butanoic acid

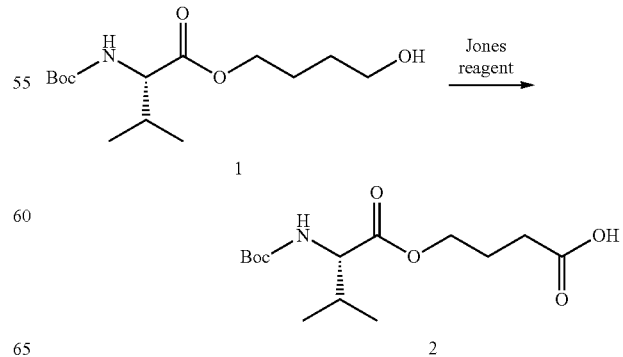

Jones reagent was added in portions to a stirred mixture of (S)-4-hydroxybutyl 2-(tert-butoxycarbonylamino)-3-methylbutanoate 1 (500 mg, 1.73 mmol) and Celite® (diatomaceous earth, 2 g) in acetone (10 mL) at 0° C. The reaction proceeded at 0° C. for over one hour and the reaction progress was monitored by TLC. After completion, the reaction was quenched with drops of PrOH, diluted with EA (10 mL) and then filtered. The filtered cake was washed with EA (5 mL) and the combined filtrate was washed with saturated brine (2 mL×2), dried over anhydrous $Na_2SO_4$, and concentrated. The residue was purified by a silica gel flash column with Hex/EA=10:1-5:1 to yield (S)-4-(2-(tert-butoxycarbonylamino)-3-methylbutanoyloxy)butanoic acid 2 (170 mg, 32%) as a white solid. $^1$H NMR was performed at 400 MHz with $CDCl_3$ as solvent to characterize the titled compound, results are as follows: δ=5.03 (d, J=9.2 Hz, 1H), 4.30-4.24 (m, 1H), 4.22-4.13 (m, 2H), 2.46 (t, J=7.4 Hz, 2H), 2.16-2.08 (m, 1H), 2.06-1.96 (m, 2H), 1.45 (s, 9H), 0.96 (d, J=6.8 Hz, 3H), 0.89 (d, J=6.4 Hz, 3H).

Step 3: Preparation of (S)-4-(2-amino-3-methylbutanoyloxy)butanoic acid

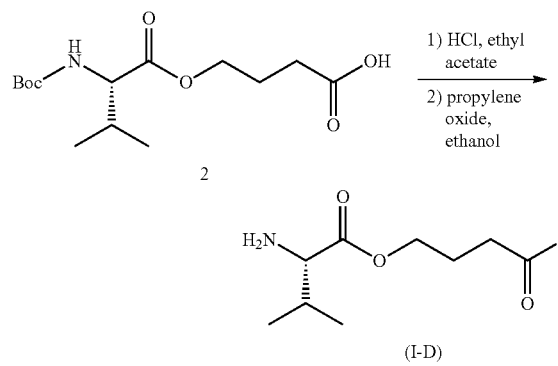

A solution of (S)-4-(2-(tert-butoxycarbonylamino)-3-methylbutanoyloxy)butanoic acid 2 (104 mg, 0.34 mmol) in HCl/EA (~2 M, 1.5 mL) was stirred at 25° C. for 24 h. After that, the reaction mixture was filtered and the resulting precipitate was collected, washed with $Et_2O$ (0.5 mL), and dried in vacuo to yield (S)-4-(2-amino-3-methylbutanoyloxy)butanoic acid (I-D) (50 mg, 71%) as a white solid in HCl salt form. $^1$H NMR was performed at 400 MHz with $CD_3OD$ as solvent to characterize the titled compound, results are as follows: δ=4.33-4.26 (m, 2H), 3.92 (d, J=4.8 Hz, 1H), 2.42 (t, J=7.2 Hz, 2H), 2.34-2.25 (m, 1H), 2.05-1.94 (m, 2H), 1.06 (d, J=6.8 Hz, 6H).

A suspension of the above white solid (800 mg, 3.3 mmol) in ethanol (4 mL) was stirred at 80° C. for around 30 min and a clear solution was formed. Then, the solution was gradually cooled to 25° C., and propylene oxide (580 mg, 10 mmol) was added dropwise. The reaction was stirred at 25° C. for 16 h, and then the resultant suspension was filtered. The white solid was collected, washed with cold ethanol, and dried in vacuo to afford (S)-4-(2-amino-3-methylbutanoyloxy)butanoic acid (I-D) (510 mg, 75%) in free base form. $^1$H NMR was performed at 400 MHz with $d_6$-DMSO as solvent to characterize the titled compound, results are as follows: δ=4.10-3.99 (m, 2H), 3.11 (d, J=5.2 Hz, 1H), 2.29 (t, J=7.4 Hz, 2H), 1.90-1.74 (m, 3H), 0.87 (d, J=6.8 Hz, 3H), 0.82 (d, J=6.4 Hz, 3H).

Example 2

Synthesis of (S)-4-(2-amino-3-methylbutanoyloxy)butanoic acid

Step 1: Preparation of benzyl 4-hydroxybutanoate

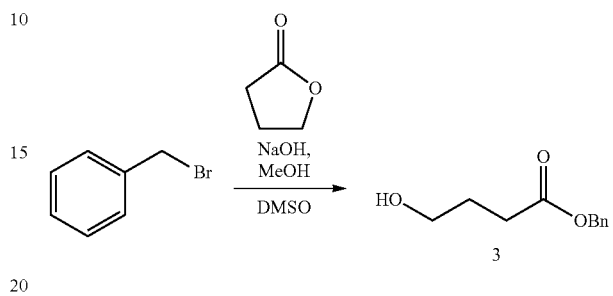

Sodium hydroxide (1.0 equivalent) was dissolved in methanol (5 volumes) with stirring while maintaining the temperature below 40° C. The reaction mixture was cooled to room temperature and butyrolactone (1.0 equivalent) was added while maintaining the temperature below 30° C., and the reaction mixture was stirred for five to six hours. The reaction mixture was concentrated in vacuo while coevaporating with tert-butyl methyl ether. The mixture was redissolved in DMSO and benzyl bromide (0.95 equivalents) was added dropwise. The reaction mixture was stirred for 3 hours at room temperature, cooled to 15° C., and quenched with purified water. The aqueous phase was washed with tert-butyl methyl ether. The collected organics were washed with water and concentrated in vacuo while coevaporating with dichloromethane to yield benzyl 4-hydroxybutanoate 3 in 69.5% yield.

Step 2: Preparation of 4-(Benzyloxy)-4-oxobutyl((benzyloxy)carbonyl)-L-valinate.

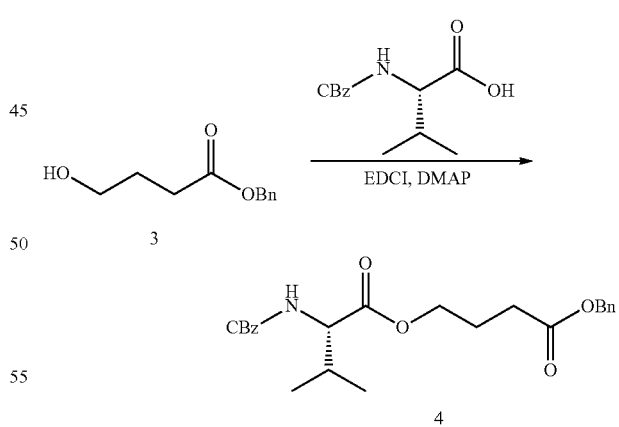

Benzyl 4-hydroxybutanoate 3 (0.95 equivalents) was dissolved in dichloromethane (2.5 volumes). CBz-L-valine (1.00 equivalent) and DMAP (0.20 equivalents) were added, followed by EDCI (1.20 equivalents) while maintaining the reaction mixture at 15° C. The reaction mixture was stirred for 20 hours at room temperature. 5% HCl (5 volumes) was added and the reaction mixture was stirred for 15 minutes at room temperature. The biphasic solution was allowed to separate, and the aqueous layer was removed. The organic layer was washed with 5% sodium bicarbonate solution and purified water, concentrated in vacuo, and suspended with silica gel (50% wt). The silica plug was washed with dichloromethane, and the combined organics were concentrated in vacuo while co-evaporating with methanol to yield 4-(benzyloxy)-4-oxobutyl((benzyloxy)carbonyl)-L-valinate 4 in 76.7% yield.

Step 3: Preparation of (S)-4-(2-amino-3-methylbutanoyloxy)butanoic acid

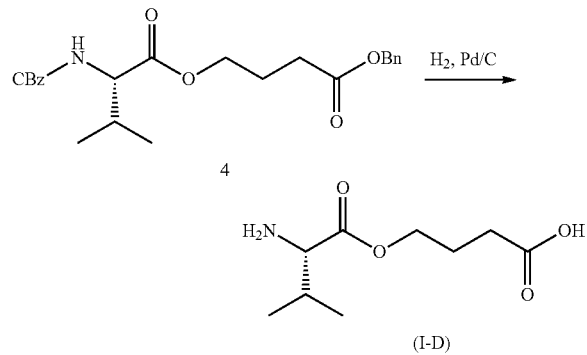

4-(Benzyloxy)-4-oxobutyl((benzyloxy)carbonyl)-L-valinate 4 (1.0 equivalent) was dissolved in methanol (5 volumes) and Pd/C (10% Pd, 15% wt) was added under a nitrogen atmosphere. The nitrogen atmosphere was replaced with a continuous flow of H₂ and the reaction mixture was stirred for 16 hours at room temperature. The reaction mixture was filtered over Celite (50% wt) and stirred for 18 hours with active carbon (25% wt). The reaction mixture was filtered over Celite® (50% wt) and the filter cake was rinsed with methanol. The reaction mixture was concentrated in vacuo while co-evaporating with methanol. The resulting residue was redissolved in tert-butyl methyl ether and stirred for 30 minutes at room temperature. Another portion of tert-butyl methyl ether (3 volumes) was added dropwise within 2 hours. The reaction mixture was stirred for four hours and filtered. The filter cake was dried in vacuo to yield (S)-4-(2-amino-3-methylbutanoyloxy)butanoic acid (I-D) in 49.6% yield.

Example 3

Synthesis of (S)-4-(2-amino-3-methylbutanoyloxy)butanoic acid

Step 1: Preparation of 4-(benzyloxy)-4-oxobutyl ((benzyloxy)carbonyl)-L-valinate

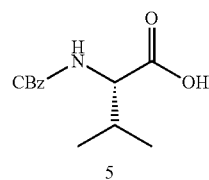

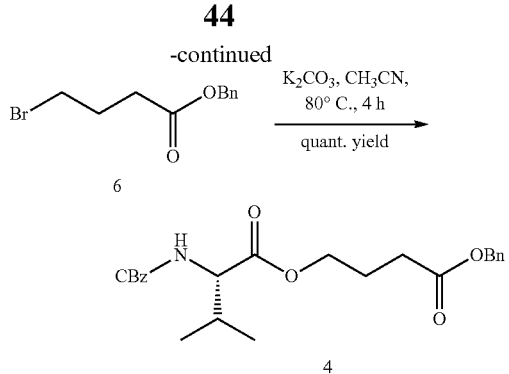

Potassium carbonate (2.0 g, 14.3 mmol, 1.5 equiv) was added to a solution of carbobenzyloxy-L-valine 5 (2.52 g, 10.0 mmol, 1.05 equiv) and benzyl 4-bromobutanoate 6 (2.46 g, 9.5 mmol, 1.0 equiv) in acetonitrile (40 mL). The reaction was warmed to 80° C. and stirred for four hours. The reaction was cooled to room temperature, filtered, and evaporated to dryness. The crude residue was dissolved in ethyl acetate and washed with a saturated sodium bicarbonate solution and brine. The organic layer was dried over magnesium sulfate, filtered, concentrated, and dried under high vacuum to yield 4-(benzyloxy)-4-oxobutyl((benzyloxy)carbonyl)-L-valinate 4 in quantitative yield. ¹H NMR was performed at 600 MHz with chloroform-d as solvent to characterize the titled compound, results are as follows: δ=7.39-7.25 (m, 10H), 5.25 (d, J=9.2 Hz, 1H), 5.15-4.98 (m, 4H), 4.27 (dd, J=9.1, 4.7 Hz, 1H), 4.22-4.03 (m, 2H), 2.43 (t, J=7.4 Hz, 2H), 2.13 (td, J=6.9, 4.7 Hz, 1H), 2.05-1.90 (m, 2H), 0.94 (d, J=6.9 Hz, 3H), 0.86 (d, J=6.9 Hz, 3H).

Step 2: Preparation of (S)-4-(2-amino-3-methylbutanoyloxy)butanoic acid

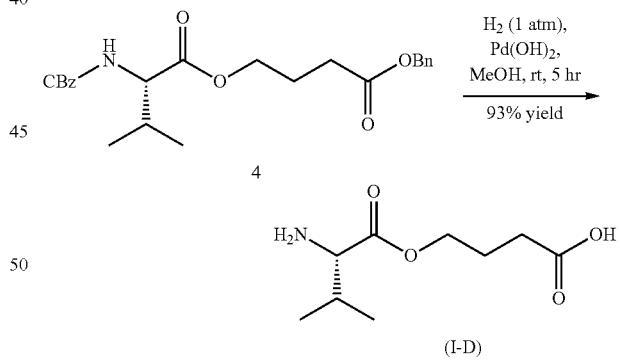

Pd(OH)₂ (5 mg) was added to a solution of 4-(benzyloxy)-4-oxobutyl((benzyloxy)carbonyl)-L-valinate 4 (100 mg, 0.2 mmol) in methanol (1 mL). The reaction was stirred at room temperature under a hydrogen atmosphere for five hours. The reaction mixture was filtered through a pad of Celite®, concentrated, and lyophilized to give (S)-4-(2-amino-3-methylbutanoyloxy)butanoic acid (I-D) in 93% yield. ¹H NMR was performed at 600 MHz with deuterium oxide as solvent to characterize the titled compound, results are as follows: δ=4.35-4.22 (m, 2H), 4.01 (d, J=4.7 Hz, 1H), 2.36 (m, J=7.1, 4.7 Hz, ¹H), 2.29 (t, J=7.3 Hz, 2H), 1.96 (m, J=6.8 Hz, 2H), 1.03 (dd, J=11.3, 7.0 Hz, 7H).

Example 4

Synthesis of (S)-4-(2-amino-3-methylbutanoyloxy)butanoic acid

Step 1: Preparation of 4-(benzyloxy)-4-oxobutyl (tert-butoxycarbonyl)-L-valinate

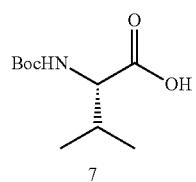

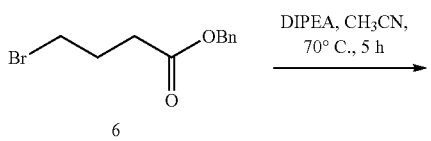

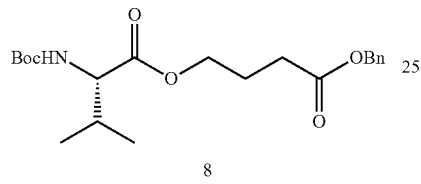

To a solution of Boc-L-Valine 7 (202 g, 930 mmol, 1.2 equiv) and benzyl 4-bromobutanoate 6 (200 g, 778 mmol, 1.0 equiv, distilled) in acetonitrile (800 mL) was added DIPEA (252 g, 1.95 mol, 2.5 equiv). The reaction mixture was heated to reflux (internal temperature 81° C.) for 3 hours. After cooling to room temperature, the reaction mixture was poured into EtOAc (~2.0 L), washed with HCl aq. (1 N, 500 mL x 3), sat. NaHCO$_3$aq (400 mL×3), and brine (200 mL), and dried over Na$_2$SO$_4$ for 2 hours. The resulting organic layer was dried over Na$_2$SO$_4$, filtered, concentrated, and dried under high vacuum to give 4-(benzyloxy)-4-oxobutyl (tert-butoxycarbonyl)-L-valinate 8 (294 g, yield: 96.4%) as a light-yellow syrup.

Step 2: Preparation of hydrochloride or trifluoroacetate salt of 4-(benzyloxy)-4-oxobutyl L-valinate

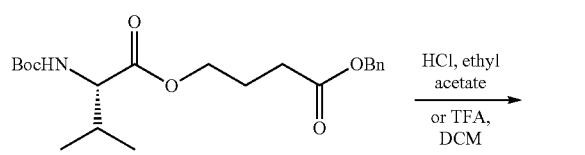

Trifluoroacetic acid (50.6 g, —6.0 equiv) was added to a solution of 4-(benzyloxy)-4-oxobutyl (tert-butoxycarbonyl)-L-valinate 8 (29.2 g, 1.0 equiv) in dichloromethane (35 mL). The reaction mixture was stirred for 24 hours at room temperature, evaporated to dryness, and co-evaporated with toluene to yield the crude trifluoroacetate salt of 4-(benzyloxy)-4-oxobutyl L-valinate 9.

Alternatively, HCl in ethyl acetate solution (2M, 500 mL, 1 mol, —5.2 equiv) was added to 4-(benzyloxy)-4-oxobutyl (tert-butoxycarbonyl)-L-valinate 8 (76.0 g, 193 mmol, 1.0 equiv) at 0° C. and the reaction mixture was allowed to stir at room temperature for 7 hours. The reaction mixture was concentrated to dryness to remove ethyl acetate to give the crude hydrochloride salt of 4-(benzyloxy)-4-oxobutyl L-valinate 9.

Step 3: Preparation of 4-(benzyloxy)-4-oxobutyl L-valinate

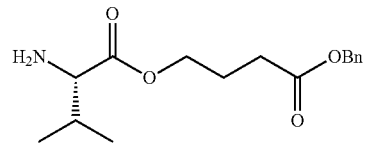

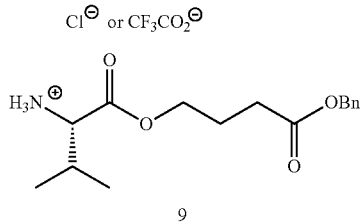

The crude trifluoroacetate salt of 4-(benzyloxy)-4-oxobutyl L-valinate 9 was dissolved in H$_2$O (350 mL). The resulting solution was washed with diethyl ether/hexane (50 mL/50 mL) and basified to pH~8 with a saturated sodium bicarbonate solution. The resulting aqueous layer was extracted with DCM (200 mL×3). The DCM layer was washed with brine, dried over Na$_2$SO$_4$, filtered, concentrated, and dried under high vacuum to give 4-(benzyloxy)-4-oxobutyl L-valinate 10 (20.0 g, yield: 92%) as a light-yellow syrup.

Alternatively, the crude hydrochloride salt of 4-(benzyloxy)-4-oxobutyl L-valinate 9 was dissolved in H$_2$O (300 mL, pH=2). The resulting aqueous solution was washed with ethyl acetate/hexane (100 mL/100 mL) twice and basified to pH~8 with 1M NaOH aq (~350 mL) at 0° C. The basic aqueous layer was then extracted with DCM (300 mL×3). The combined DCM layer was washed with brine, dried over Na$_2$SO$_4$, filtered, concentrated, and dried under high vacuum to give 4-(benzyloxy)-4-oxobutyl L-valinate 10 (55.6 g, yield: 99%) as a light-yellow syrup.

Step 4: Purification of 4-(benzyloxy)-4-oxobutyl L-valinate

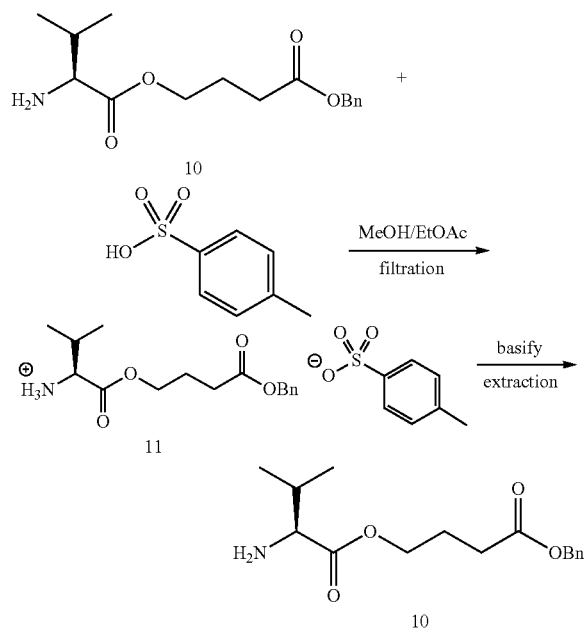

15 g of 4-(Benzyloxy)-4-oxobutyl L-valinate 10 was dissolved in MTBE (70 mL). p-toluenesulfonic acid (pTSA) solution in MTBE (10.68 g, 56.2 mmol, 1.0 eq, in 120 mL MTBE) was added and the resulting white suspension was stirred overnight. The white solid product was collected by filtration, washed with MTBE (20 mL×3), and dried under high vacuum to give the para-toluenesulfonate salt of 4-(benzyloxy)-4-oxobutyl L-valinate 11 (23.2 g, 92% yield, 98% purity by HPLC). Intermediate 11 could be further purified by recrystallization in ethyl acetate. Intermediate 11 was dissolved in H₂O (120 mL) and basified to pH~8 with solid NaHCO₃. The aqueous solution was extracted with DCM (50 mL×3), and the organic layers were combined, dried over Na₂SO₄, filtered, and concentrated to furnish 21 g of 4-(benzyloxy)-4-oxobutyl L-valinate 10 in upgraded purity.

This purification can be performed with a variety of acids as summarized below in Table 1.

TABLE 1

Purification with various acids.

| Acid | MW of Acid | Mole eq of Amine to Acid | Melting Point of salt | Yield |
|---|---|---|---|---|
| Oxalic Acid | 90 | 1:1 | 130-132.5° C. | 92% |
| L-Tartaric Acid | 150 | 1:1 | 72.8-74.2° C. | — |
| TsOH•H₂O | 190 | 1:1 | 105-106.5° C. | 92% |
| Benzoic Acid | 122.12 | 1:1 | 64.2-64.5° C. | 61% |
| Lactic Acid | 90.08 | 1:1 | colorless oil | 93% |
| Acetic Acid | 60.05 | 1:1 | colorless solution | 94% |
| Citric Acid | 192.12 | 1:1 | colorless syrup | 86% |
| Citric Acid | 192.12 | 2:1 | colorless syrup | 88% |
| Citric Acid | 192.12 | 3:1 | colorless syrup | 87% |
| DL-Camphorsulfonic Acid | 232.08 | 1:1 | colorless syrup | 81% |

Step 5: Preparation of (S)-4-(2-amino-3-methylbutanoyloxy)butanoic acid

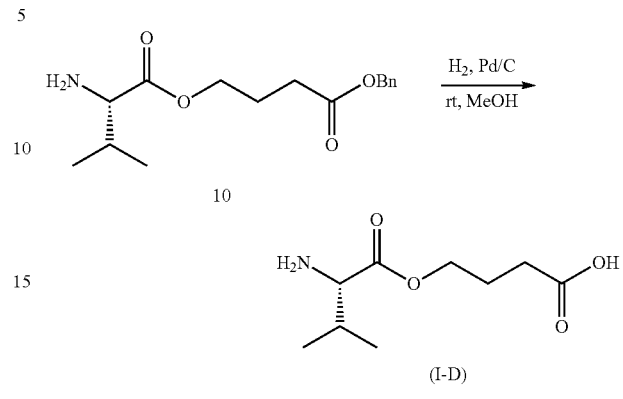

Pd/C (catalytic amount) was added to a solution of 4-(benzyloxy)-4-oxobutyl L-valinate 10 in methanol (0.2 M). The reaction was stirred at room temperature under a hydrogen atmosphere for five hours. The reaction mixture was filtered through a pad of Celite®, concentrated, and lyophilized to give (S)-4-(2-amino-3-methylbutanoyloxy)butanoic acid (I-D).

Example 5

Synthesis of (S)-4-(2-amino-3-methylbutanoyloxy)butanoic acid

Step 1: Preparation of 4-(benzyloxy)-4-oxobutyl (tert-butoxycarbonyl)-L-valinate

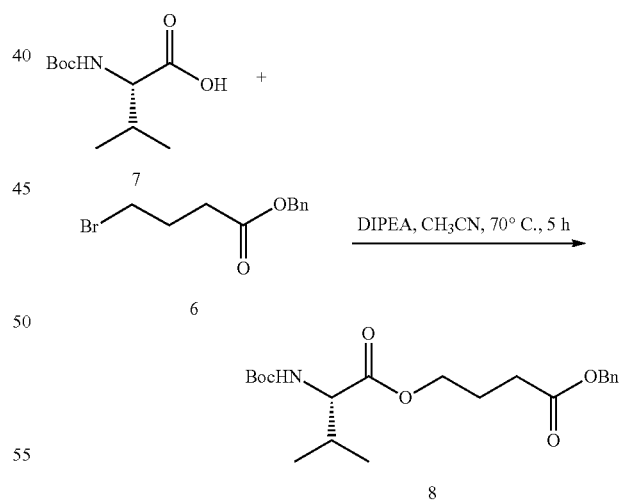

Alternatively, to a solution of Boc-L-Valine 7 (1.187 kg, 5.461 mol, 1.2 equiv) and benzyl 4-bromobutanoate 6 (1170 g, 4.55 mol, 1.0 equiv) in acetonitrile (4680 mL) was added DIPEA (1.469 kg, 11.38 mol, 2.5 equiv). The reaction mixture was heated to reflux (internal temperature 81° C.) for 3 hours, and then more DIPEA (223 g, 1.72 mol, 0.3 equiv) was added. The reaction mixture was heated to reflux (internal temperature 81° C.) for another 3 hours. After cooling to room temperature, the reaction mixture was poured into EtOAc (~9.4 L), washed with HCl aq. (2 N, 2000 mL×2), sat. NaHCO₃ aq. (600 mL×3), and brine (500 mL×1), and dried over Na₂SO₄ for 2 hours. The resulting organic layer was dried over Na₂SO₄, filtered, concentrated, and dried under high vacuum to give crude 4-(benzyloxy)-4-oxobutyl (tert-butoxycarbonyl)-L-valinate 8 (1730 g) as a light-yellow syrup.

Step 2: Preparation of Hydrochloride or Trifluoroacetate Salt of 4-(benzyloxy)-4-oxobutyl L-valinate

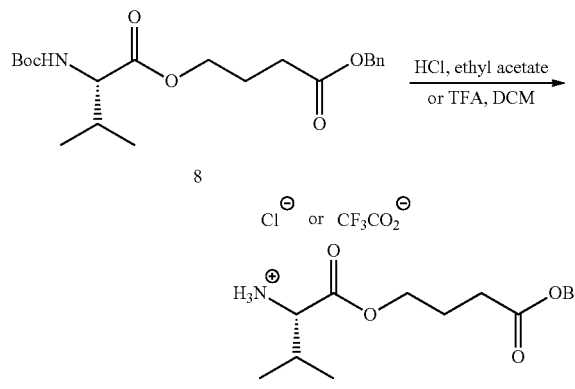

Alternatively, HCl in ethyl acetate solution (2 M, 6885 mL, 13.771 mol, ~6.0 eq) was added to 4-(benzyloxy)-4-oxobutyl (tert-butoxycarbonyl)-L-valinate 8 (902.0 g, 2.295 mol) at 0° C. and the reaction mixture was allowed to stir at room temperature for 6 hours. The reaction mixture was concentrated to dryness to remove ethyl acetate to give the crude hydrochloride salt of 4-(benzyloxy)-4-oxobutyl L-valinate 9.

Step 3: Preparation of 4-(benzyloxy)-4-oxobutyl L-valinate

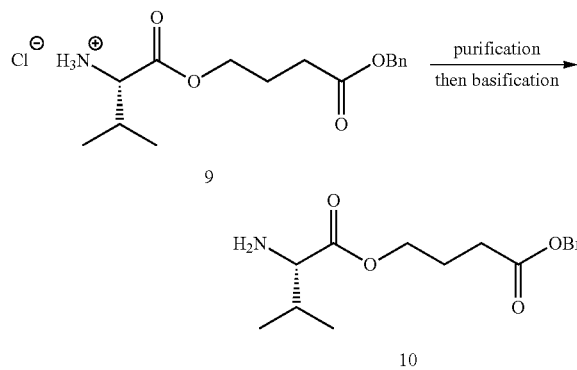

Alternatively, the crude salt of 4-(benzyloxy)-4-oxobutyl L-valinate 9 was dissolved in H₂O (5900 mL, pH=2). The resulting aqueous solution was washed with ethyl acetate (900 mL) and basified to pH~8 with sat. NaHCO₃aq (~4000 mL) at room temperature. The basic aqueous layer was then extracted with EtOAc (2700 mL×3). The combined EtOAc layer was washed with water (900 mL) and brine (900 mL), dried over Na₂SO₄ for 2 hours, and filtered to give a solution of 4-(benzyloxy)-4-oxobutyl L-valinate 10 (~9 L).

Step 4: Purification of 4-(benzyloxy)-4-oxobutyl L-valinate

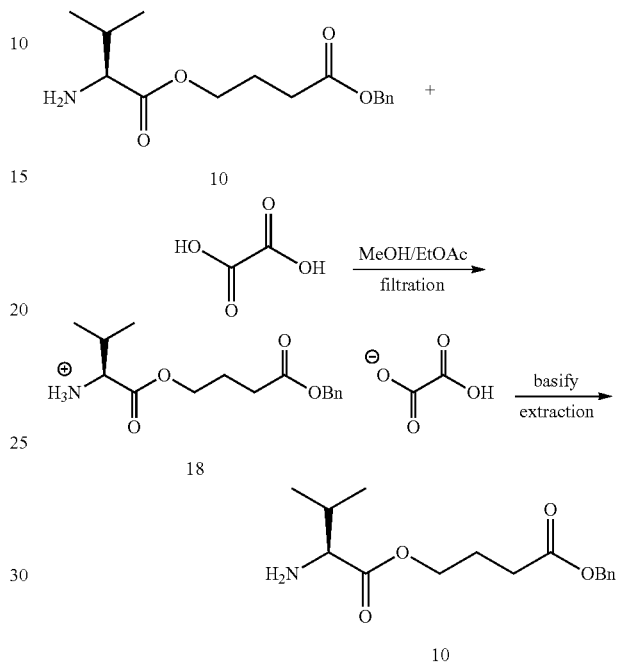

Alternatively, a solution of oxalic acid (205.6 g, 2.3 mol) in 2700 mL MeOH was slowly added to the solution of 4-(benzyloxy)-4-oxobutyl L-valinate 10 (97.8% purity from 902.0 g of 4-(benzyloxy)-4-oxobutyl (tert-butoxycarbonyl)-L-valinate 8) at 30° C. A white solid precipitated after ten minutes. MeOH (675 mL) and EtOAc (2700 mL) were added, and the resulting solution was stirred at 60° C. for 1 hour and gradually cooled to room temperature. The white solid product was collected by filtration, washed with ethyl acetate (1800 mL×2), and dried under high vacuum to give the oxalic acid salt of 4-(benzyloxy)-4-oxobutyl L-valinate 18 in 98.4% purity. The oxalic acid salt of 4-(benzyloxy)-4-oxobutyl L-valinate 18 (16.0 g) was dissolved in sat. NaHCO₃aq (~150 mL) and basified to pH~8 at room temperature to give a cloudy suspension. The basic aqueous layer was extracted with EtOAc (150 mL×3). The combined EtOAc layer was washed with 250 mL sat. brine, dried over Na₂SO₄, filtered, concentrated, and dried under high vacuum to give crude 4-(benzyloxy)-4-oxobutyl L-valinate 10 (11.0 g, 90% yield) as a colorless oil.

Step 5: Preparation of (S)-4-(2-amino-3-methylbutanoyloxy)butanoic acid

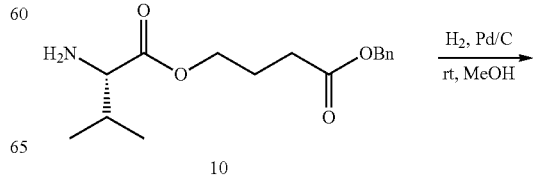

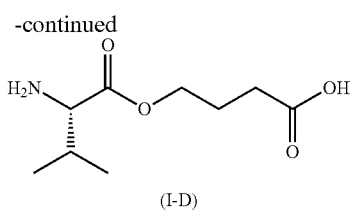

(I-D)

Alternatively, Pd/C (0.22 g, 2% in weight) was added to a solution of 4-(benzyloxy)-4-oxobutyl L-valinate 10 (11.0 g, 37.5 mmol) in methanol (40 mL). The reaction mixture was charged with $H_2$ three times and hydrogenated at 60 psi with a Parr shaker for 2 hours. The reaction mixture was filtered through a pad of Celite®, and the pad of Celite® was washed with 50 mL of methanol. 2-Methyl-THF (70 mL) was slowly added to the filtrate. The resulting white suspension was stirred overnight, filtered, and dried under high vacuum to give (S)-4-(2-amino-3-methylbutanoyloxy)butanoic acid (I-D) (5.41 g, 71% yield) as a white solid. (S)-4-(2-amino-3-methylbutanoyloxy)butanoic acid (I-D) (3.3 g) was further triturated in methanol (23 mL). 2-Methyl-THF was then added slowly (33 mL) and the resulting mixture was stirred for 18 hours. The white suspension was filtered, washed with 2-methyl-THF slowly (6.6 mL×3), and dried under high vacuum to give (S)-4-(2-amino-3-methylbutanoyloxy)butanoic acid (I-D) (2.52 g, 76% yield) as a white solid.

Example 6

Synthesis of (S)-4-(2-amino-3-methylbutanoyloxy)butanoic acid

Step 1: Preparation of Protected 4-(benzyloxy)-4-oxobutyl L-valinate

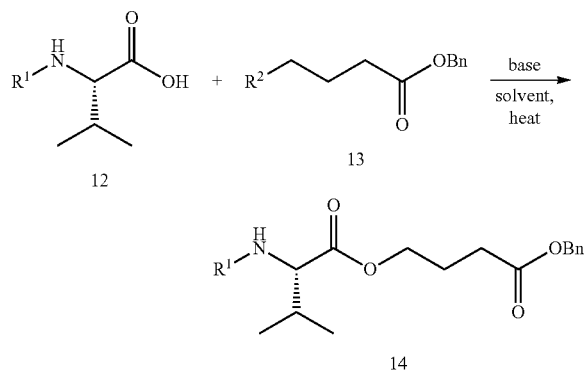

Base (1.5 equiv) was added to a solution of protected L-valine 12 (1.05 equiv) and activated benzyl butanoate 13 (1.0 equiv) in acetonitrile (0.25 M). The reaction was warmed to 70° C. and stirred for five hours. The reaction was cooled to room temperature, filtered, and evaporated to dryness. The crude residue was dissolved in ethyl acetate and washed with a saturated sodium bicarbonate solution and brine. The organic layer was dried over magnesium sulfate, filtered, concentrated, and dried under high vacuum to yield protected 4-(benzyloxy)-4-oxobutyl L-valinate 14.

$R^1$ was selected from Fmoc and Dtb-Fmoc. $R^2$ was selected from OTs, OMs, Cl, I, and Br. The base was selected from N,N-diisopropylethylamine, triethylamine, potassium carbonate, sodium carbonate, and sodium bicarbonate. The solvent was selected from acetonitrile, propionitrile, tetrahydrofuran, dichloromethane, dimethylformamide, and dimethyl sulfoxide.

Step 2: Preparation of Salt of 4-(benzyloxy)-4-oxobutyl L-valinate

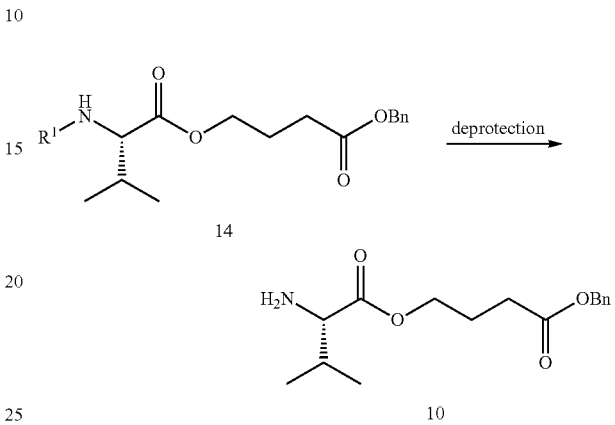

Base (3.0 equiv) was added to a solution of protected 4-(benzyloxy)-4-oxobutyl L-valinate 14 (1.0 equiv) in dichloromethane (0.2 M). The reaction mixture was stirred for four hours at room temperature, washed with a saturated sodium bicarbonate solution and brine, dried over magnesium sulfate, filtered, concentrated, and dried under high vacuum to yield 4-(benzyloxy)-4-oxobutyl L-valinate 10.

The base was selected from piperidine, 1,8-diazabicyclo [5.4.0]undec-7-ene, and N,N-diisopropylethylamine.

Step 3: Preparation of (S)-4-(2-amino-3-methylbutanoyloxy)butanoic acid

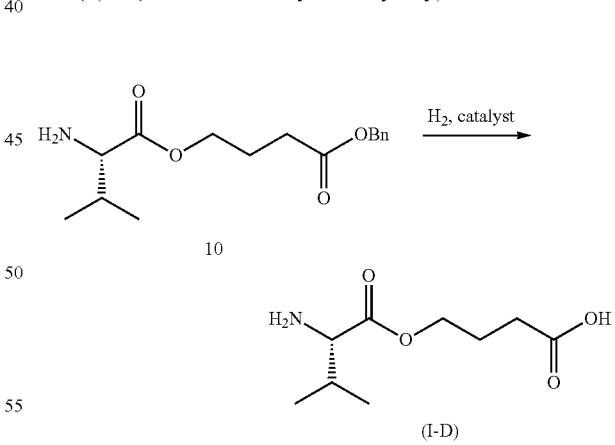

Catalyst was added to a solution of 4-(benzyloxy)-4-oxobutyl L-valinate 10 in methanol (0.2 M). The reaction was stirred at room temperature under a hydrogen atmosphere for five hours. The reaction mixture is filtered through a pad of Celite®, concentrated, and lyophilized to give (S)-4-(2-amino-3-methylbutanoyloxy)butanoic acid (I-D).

The catalyst was selected from Pd/C, Pd(OH)$_2$, Pd/Al$_2$O$_3$, Pd(OAc)$_2$/Et$_3$SiH, (PPh$_3$)$_3$RhCl, and PtO$_2$.

Example 7

Synthesis of (S)-4-(2-amino-3-methylbutanoyloxy)butanoic acid

Step 1: Preparation of 4-hydroxybutyl ((benzyloxy)carbonyl)-L-valinate

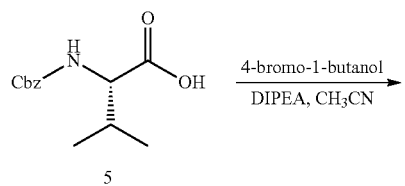

4-Bromo-1-butanol (0.5 g, 3.3 mmol, 0.9 equiv) and DIPEA (0.7 g, 5.4 mmol, 1.5 equiv) were added to a solution of Cbz-Val-OH 5 (1.0 g, 4.0 mmol) in CH$_3$CN (10 mL). The reaction mixture was stirred at 80° C. for 8 hours, concentrated, and redissolved in EtOAc. The resulting solution was washed with water, a saturated NaHCO$_3$ solution, and brine. The organic layer was dried over MgSO$_4$, filtered, and concentrated to afford 4-hydroxybutyl ((benzyloxy)carbonyl)-L-valinate 15 in quantitative yield. The product was carried forward to the next step without further purification. $^1$H NMR (500 MHz, CDCl$_3$) δ 7.38-7.25 (m, 5H), 6.20 (d, J=8.9 Hz, 1H), 5.10 (d, J=11.7 Hz, 1H), 5.04 (d, J=11.8 Hz, 1H), 4.43 (dd, J=9.1, 6.5 Hz, 1H), 4.23 (t, J=7.3 Hz, 1H), 4.22-4.13 (m, 1H), 4.06-3.97 (m, 1H), 3.70-3.55 (m, 2H), 2.41-2.28 (m, J=6.6 Hz, 1H), 1.78-1.53 (m, 4H), 0.96 (dd, J=25.0, 6.7 Hz, 6H). LCMS (ESI): m/z calculated for [C$_{17}$H$_{25}$NO$_5$+H]$^+$324.18, found 324.25 [M+H]$^+$.

Step 2: Preparation of 4-((((benzyloxy)carbonyl)-L-valyl)oxy)butanoic acid

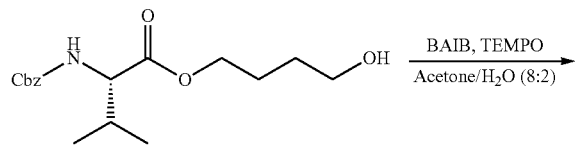

Bis(acetoxy)iodobenzene (BAIB) (2.2 g, 6.8 mmol, 2.2 equiv) and TEMPO (0.1 g, 0.6 mmol, 0.2 equiv) were added to a solution of 4-hydroxybutyl ((benzyloxy)carbonyl)-L-valinate 15 (1 g, 3.1 mmol) in acetone/H$_2$O (10 mL, 8:2). The reaction was stirred at room temperature for 8 hours. The reaction was quenched with i-PrOH and stirred for 2 hours. The reaction was diluted with EtOAc and washed with 1N HCl, H$_2$O, and brine. The organic layer was dried over MgSO$_4$, filtered, concentrated, and purified by flash column chromatography to afford 4-((((benzyloxy)carbonyl)-L-valyl)oxy)butanoic acid 16 in 83% yield. $^1$H NMR (500 MHz, CDCl$_3$) δ 7.38-7.25 (m, 5H), 6.05 (d, J=9.0 Hz, 1H), 5.10 (d, J=11.6 Hz, 1H), 5.04 (d, J=11.7 Hz, 1H), 4.44 (dd, J=9.2, 6.6 Hz, 1H), 4.25 (dt, J=11.5, 6.2 Hz, 1H), 4.15 (dt, J=11.5, 6.2 Hz, 1H), 2.50-2.34 (m, 2H), 2.32-2.18 (m, J=6.7 Hz, 1H), 2.11-1.99 (m, 1H), 1.93 (tdd, J=14.0, 7.0, 6.0 Hz, 1H), 0.97 (dd, J=24.9, 6.6 Hz, 6H). LCMS (ESI): m/z calculated for [C$_{17}$H$_{23}$NO$_6$—H]$^-$336.14, found 336.23 [IVI-H]$^-$.

Step 3: Preparation of (S)-4-(2-amino-3-methylbutanoyloxy)butanoic acid

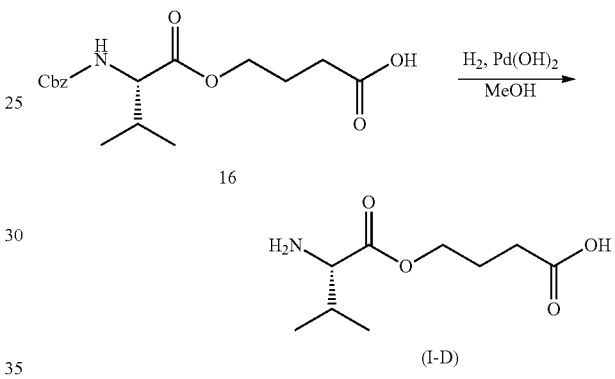

Pd(OH)$_2$ was added to a solution of 4-((((benzyloxy)carbonyl)-L-valyl)oxy)butanoic acid 16 (1.5 g, 4.4 mmol) in MeOH (10 mL). The reaction was stirred for 3 hours under an H$_2$ atmosphere and filtered through a pad of Celite®. MTBE was added and the reaction mixture was stirred vigorously to afford a white solid. The solid was filtered and dried under vacuum to afford (S)-4-(2-amino-3-methylbutanoyloxy)butanoic acid (I-D) in quantitative yield. $^1$H NMR (600 MHz, D$_2$O) δ 4.35-4.22 (m, 2H), 4.01 (d, J=4.7 Hz, 1H), 2.36 (pd, J=7.1, 4.7 Hz, 1H), 2.29 (t, J=7.3 Hz, 2H), 1.96 (p, J=6.8 Hz, 2H), 1.03 (dd, J=11.3, 7.0 Hz, 7H). LCMS (ESI): m/z calculated for [C$_9$H$_{17}$NO$_4$+H]$^+$204.12, found 204.21 [M+H]$^+$.

Example 8

Synthesis of (S)-4-(2-amino-3-methylbutanoyloxy)butanoic acid

Step 1: Preparation of 4-(tert-butoxy)-4-oxobutyl ((benzyloxy)carbonyl)-L-valinate

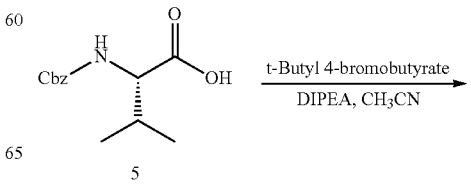

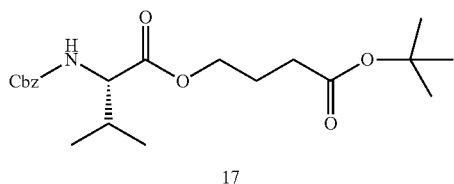

17 tert-Butyl 4-bromobutyrate (0.4 g, 1.8 mmol, 0.9 equiv) and DIPEA (0.4 g, 3.0 mmol, 1.5 equiv) were added to a solution of Cbz-Val-OH 5 (0.5 g, 2.0 mmol) in CH$_3$CN (5 mL). The reaction mixture was stirred at 80° C. for 8 hours, concentrated, and redissolved in EtOAc. The resulting solution was washed with water, a saturated NaHCO$_3$ solution, and brine. The organic layer was dried over MgSO$_4$, filtered, and concentrated to afford 4-(tert-butoxy)-4-oxobutyl ((benzyloxy)carbonyl)-L-valinate 17 in quantitative yield, which was carried forward to the next step without further purification. $^1$H NMR (500 MHz, CDCl$_3$) δ 7.37-7.26 (m, 5H), 6.01 (d, J=9.1 Hz, 1H), 5.13-5.02 (m, 2H), 4.45 (dd, J=9.2, 6.6 Hz, 1H), 4.22 (dt, J=11.5, 6.0 Hz, 1H), 4.11 (dt, J=11.5, 6.0 Hz, 1H), 2.45 (qt, J=15.2, 7.1 Hz, 2H), 2.12 (dq, J=13.4, 6.7 Hz, 1H), 2.07-1.88 (m, 2H), 1.42 (s, 7H), 0.99 (dd, J=25.0, 6.7 Hz, 6H). LCMS (ESI): m/z calculated for [C$_{21}$H$_{31}$NO$_6$+H]$^+$394.22, found 394.38 [M+H]$^+$.

Step 2: Preparation of 4-((((benzyloxy)carbonyl)-L-valyl)oxy)butanoic acid

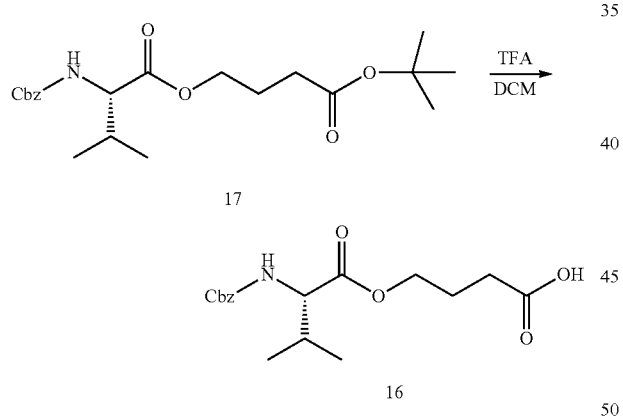

TFA (1.5 g, 13 mmol, 10 equiv) was added to a solution of 4-(tert-butoxy)-4-oxobutyl ((benzyloxy)carbonyl)-L-valinate 17 (0.5 g, 1.3 mmol) in DCM (5 mL). The reaction mixture was stirred at room temperature for 2 hours and evaporated to dryness. The resulting residue was co-evaporated with toluene to afford 4-((((benzyloxy)carbonyl)-L-valyl)oxy)butanoic acid 16 in quantitative yield. $^1$H NMR (500 MHz, CDCl$_3$) δ 7.38-7.25 (m, 5H), 6.05 (d, J=9.0 Hz, 1H), 5.10 (d, J=11.6 Hz, 1H), 5.04 (d, J=11.7 Hz, 1H), 4.44 (dd, J=9.2, 6.6 Hz, 1H), 4.25 (dt, J=11.5, 6.2 Hz, 1H), 4.15 (dt, J=11.5, 6.2 Hz, 1H), 2.50-2.34 (m, 2H), 2.32-2.18 (m, J=6.7 Hz, 1H), 2.11-1.99 (m, 1H), 1.93 (tdd, J=14.0, 7.0, 6.0 Hz, 1H), 0.97 (dd, J=24.9, 6.6 Hz, 6H). LCMS (ESI): m/z calculated for [C$_{17}$H$_{23}$NO$_6$+H]$^+$338.16, found 338.31 [M+H]$^+$.

Step 3: Preparation of (S)-4-(2-amino-3-methylbutanoyloxy)butanoic acid

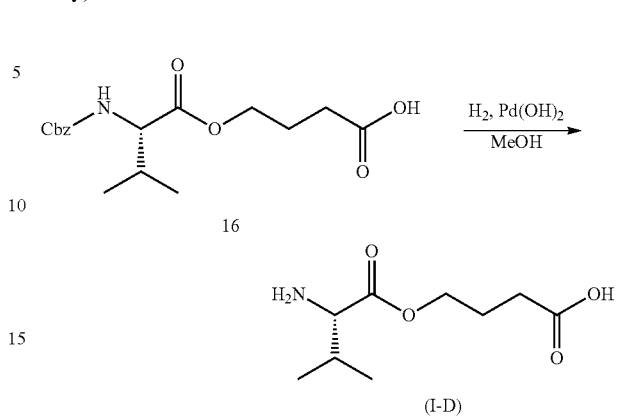

Pd(OH)$_2$ was added to a solution of 4-((((benzyloxy)carbonyl)-L-valyl)oxy)butanoic acid 16 (0.5 g, 1.5 mmol) in MeOH (5 mL). The reaction mixture was stirred for 3 hours under an H$_2$ atmosphere, filtered through a pad of Celite®, and concentrated to afford (S)-4-(2-amino-3-methylbutanoyloxy)butanoic acid (I-D) in quantitative yield. $^1$H NMR (600 MHz, D$_2$O) δ 4.35-4.22 (m, 2H), 4.01 (d, J=4.7 Hz, 1H), 2.36 (pd, J=7.1, 4.7 Hz, 1H), 2.29 (t, J=7.3 Hz, 2H), 1.96 (p, J=6.8 Hz, 2H), 1.03 (dd, J=11.3, 7.0 Hz, 7H). LCMS (ESI): m/z calculated for [C$_9$H$_{17}$NO$_4$+H]$^+$204.12, found 204.21 [M+H]$^+$.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It was intended that the following claims define the scope of the invention and that methods and structures within the scope of these claims and their equivalents be covered thereby.

What is claimed is:

1. A method of preparing a compound of Formula (I-D):

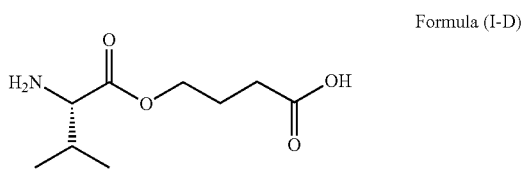

Formula (I-D)

or a pharmaceutically acceptable salt thereof, comprising contacting a compound of Formula (I-H):

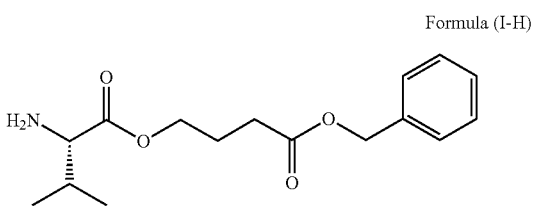 [SMILES: CC(C)[C@H](N)C(=O)OCCCC(=O)OCc1ccccc1]

Formula (I-H)

with gaseous hydrogen in the presence of a catalyst and a solvent.

2. The method of claim 1, wherein the catalyst is selected from a Pd-, a Rh-, and a Pt-based catalyst.

3. The method of claim 1, wherein the catalyst is selected from Pd/C, Pd(OH)$_2$, Pd/Al$_2$O$_3$, Pd(OAc)$_2$/Et$_3$SiH, (PPh$_3$)$_3$RhCl, and PtO$_2$.

4. The method of claim 1, wherein the catalyst is Pd/C.

5. The method of claim 1, wherein the solvent is selected from methanol, ethanol, diethyl ether, methyl tert-butyl ether, tetrahydrofuran, and dichloromethane.

6. A method of preparing a compound of Formula (I-H):

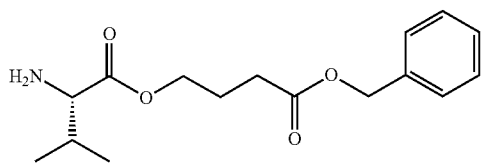

Formula (I-H)

comprising contacting a compound of Formula (I-F):

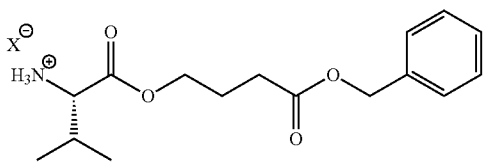

Formula (I-F)

with a base, wherein X$^-$ is Cl.

7. The method of claim 6, wherein the base is selected from sodium hydroxide, potassium carbonate, sodium carbonate, sodium bicarbonate, ammonium bicarbonate, and ammonium carbonate.

8. The method of claim 6, wherein the base is sodium bicarbonate.

9. A method of preparing a compound of Formula (I-F):

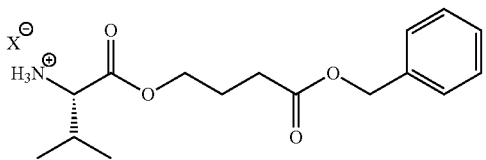

Formula (I-F)

comprising contacting a compound of Formula (I-G):

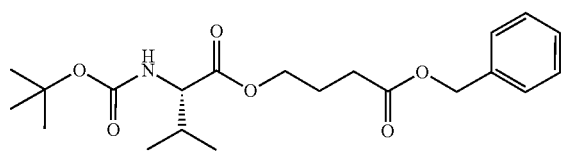

Formula (I-G)

with hydrochloric acid in the present of a solvent, wherein X$^-$ is Cl.

10. The method of claim 9, wherein the solvent is selected from dichloromethane, ethyl acetate, and methyl tert-butyl ether.

11. A method of preparing a compound of Formula (I-A):

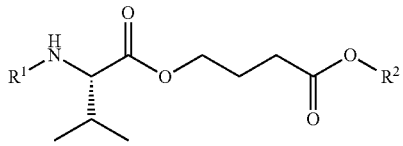

Formula (I-A)

wherein R$^1$ is tert-butoxy carbonyl; and R$^2$ is benzyl, comprising contacting a compound of Formula (I-B):

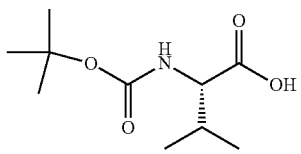

Formula (I-B)

with a compound of Formula (I-C):

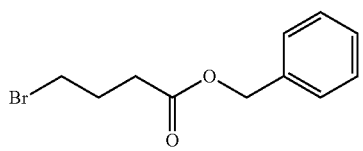

Formula (I-C)

in the presence of a base and a solvent, wherein the base is selected from N,N-diisopropylethylamine, triethylamine, potassium carbonate, sodium carbonate, and sodium bicarbonate.

12. The method of claim 11, wherein the base is N,N-diisopropylethylamine.

13. The method of claim 11, wherein the solvent is selected from acetonitrile, propionitrile, tetrahydrofuran, dichloromethane, dimethylformamide, dimethyl sulfoxide, and toluene.

14. The method of claim 11, wherein the solvent is toluene.

15. A method of preparing a compound of Formula (I-D):

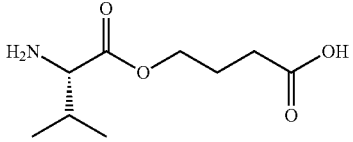

Formula (I-D)

comprising the steps of:
(a) contacting a compound of Formula (I-B):

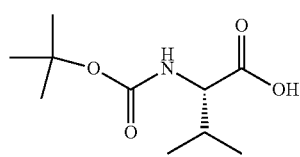

Formula (I-B)

with a compound of Formula (I-C):

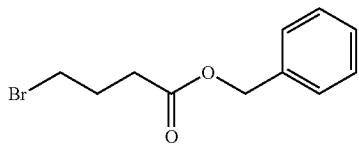

Formula (I-C)

in the presence of a base and a solvent to provide a compound of Formula (I-A):

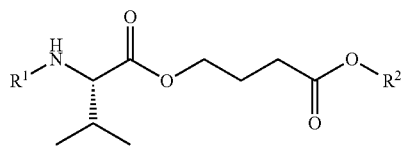

Formula (I-A)

wherein R¹ is tert-butoxy carbonyl; and R² is benzyl;
(b) reacting a compound of Formula (I-G):

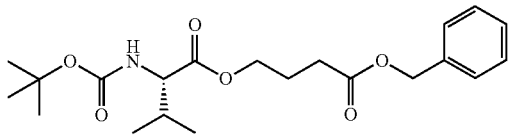

Formula (I-G)

with hydrochloric acid in the present of a solvent, wherein X⁻ is Cl, to provide a compound of Formula (I-F):

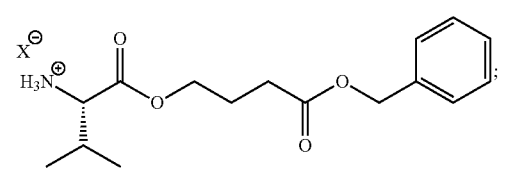

Formula (I-F)

(c) reacting a compound of Formula (I-F):

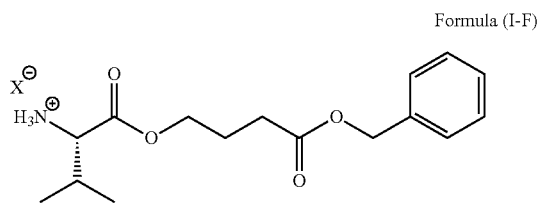

Formula (I-F)

with a base, wherein X⁻ is Cl; to provide a compound of Formula (I-H):

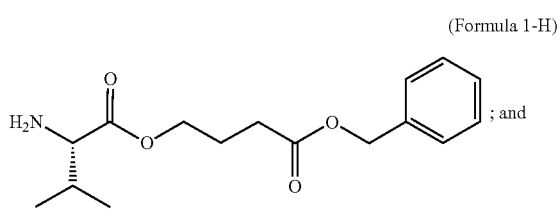 [SMILES: CC(C)[C@H](N)C(=O)OCCCC(=O)OCc1ccccc1]

(Formula 1-H)

; and (d) reacting a compound of Formula (I-H):

Formula (I-H)

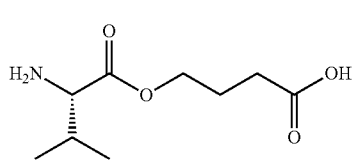

with gaseous hydrogen in the presence of a catalyst and a solvent, to provide a compound of Formula (I-D):

Formula (I-D)

or a pharmaceutically acceptable salt thereof.

16. The method of claim 15, wherein,
in step (a) the base is N,N-diisopropylethylamine and the solvent is toluene;
in step (c) the base is sodium bicarbonate; and
in step (d) the catalyst is Pd/C.

* * * * *